(12) United States Patent
Druyan et al.

(10) Patent No.: US 8,624,787 B2
(45) Date of Patent: Jan. 7, 2014

(54) WEARABLE ANTENNA ASSEMBLY FOR AN IN-VIVO DEVICE

(75) Inventors: Yosef Druyan, Petach Tikva (IL); Vitaly Fastovsky, Haifa (IL); Zvika Gilad, Haifa (IL)

(73) Assignee: Given Imaging Ltd., Yoqneam (IL)

( * ) Notice: Subject to any disclaimer, the term of this patent is extended or adjusted under 35 U.S.C. 154(b) by 122 days.

(21) Appl. No.: 13/208,783

(22) Filed: Aug. 12, 2011

(65) Prior Publication Data

US 2013/0038493 A1     Feb. 14, 2013

(51) Int. Cl.
*H01Q 1/12* (2006.01)
(52) U.S. Cl.
USPC ............................................. 343/718
(58) Field of Classification Search
USPC .................................. 343/718, 702
See application file for complete search history.

(56) References Cited

U.S. PATENT DOCUMENTS

| | | | |
|---|---|---|---|
| 5,374,934 A | 12/1994 | Miura | |
| 6,553,247 B1 | 4/2003 | Rytky | |
| 6,934,573 B1 * | 8/2005 | Glukhovsky et al. | 600/407 |
| 7,150,048 B2 | 12/2006 | Buckman | |
| 2005/0222490 A1 * | 10/2005 | Glukhovsky et al. | 600/102 |
| 2006/0169292 A1 | 8/2006 | Iddan | |
| 2006/0238433 A1 | 10/2006 | Chou | |
| 2007/0268190 A1 | 11/2007 | Huynh | |
| 2008/0147188 A1 * | 6/2008 | Steinberg | 623/17.11 |
| 2010/0289712 A1 | 11/2010 | Zheng | |

OTHER PUBLICATIONS

International Search Report for International Application No. PCT/IL2012/050308 mailed Dec. 27, 2012.

\* cited by examiner

*Primary Examiner* — Huedung Mancuso
(74) *Attorney, Agent, or Firm* — Pearl Cohen Zedek Latzer Baratz, LLP

(57) ABSTRACT

A wearable antenna assembly includes a posterior antenna assembly and an anterior antenna assembly. The posterior antenna assembly may include a posterior base that includes a lateral portion having a lateral line, and one or two protrusions that continue from the lateral portion and extend away from it, and one or more antenna elements that are formed in the respective protrusion. The protrusions may be configured such that each antenna element lies on the buttocks and is situated adjacent to, or in front of, a greater sciatic notch of the pelvis. The anterior antenna assembly may include an anterior lateral base having a lateral line, and n antenna elements that are formed in the anterior lateral base along the lateral line. The anterior lateral base may be configured such that, when the belt is worn, the n antenna elements are situated adjacent to, or in front of, the abdomen. The orientations of the antenna elements may be optimized to maximize reception of signals originating from a swallowed in-vivo device.

21 Claims, 15 Drawing Sheets

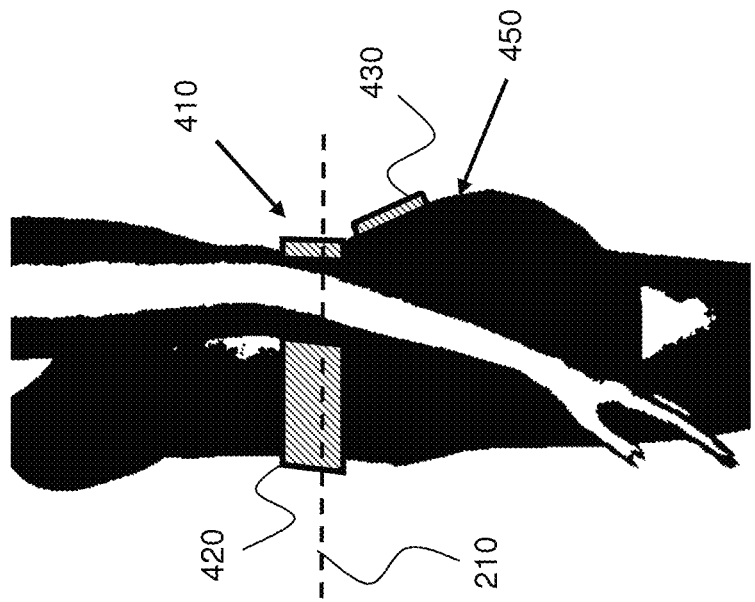
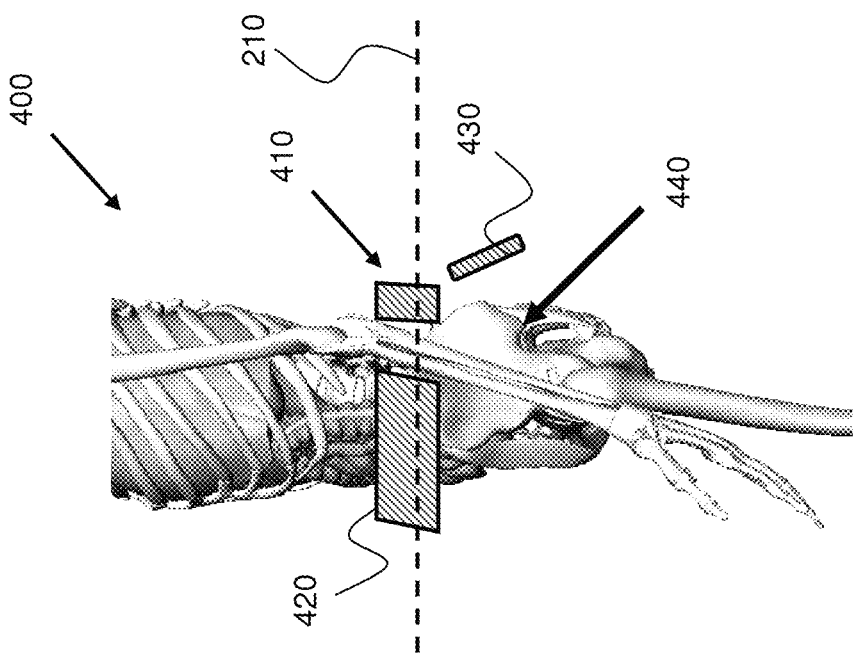

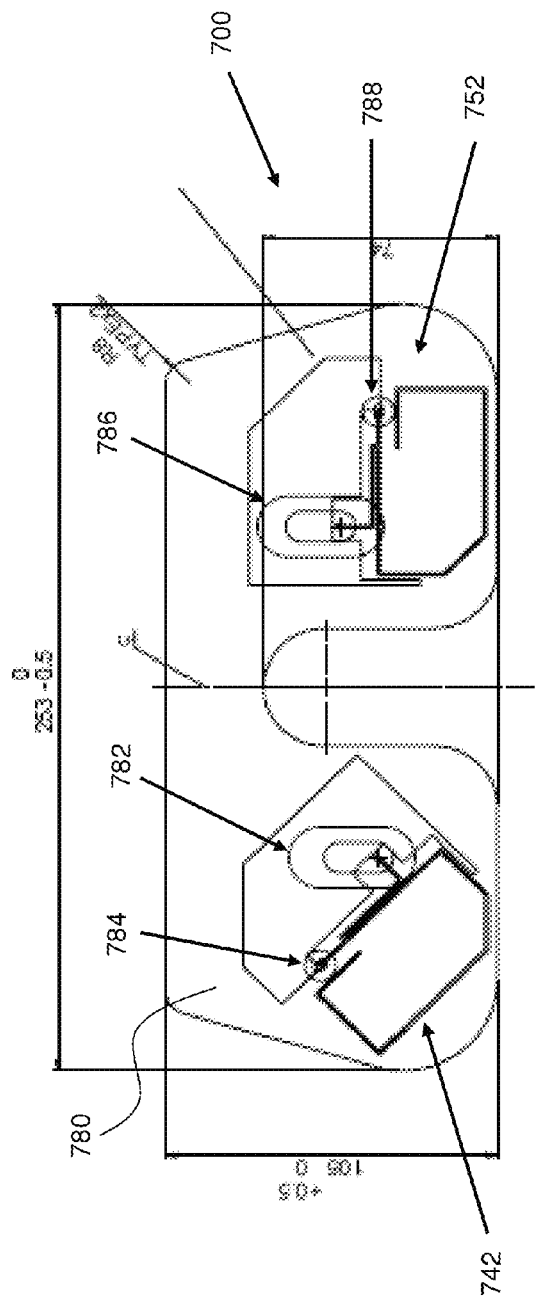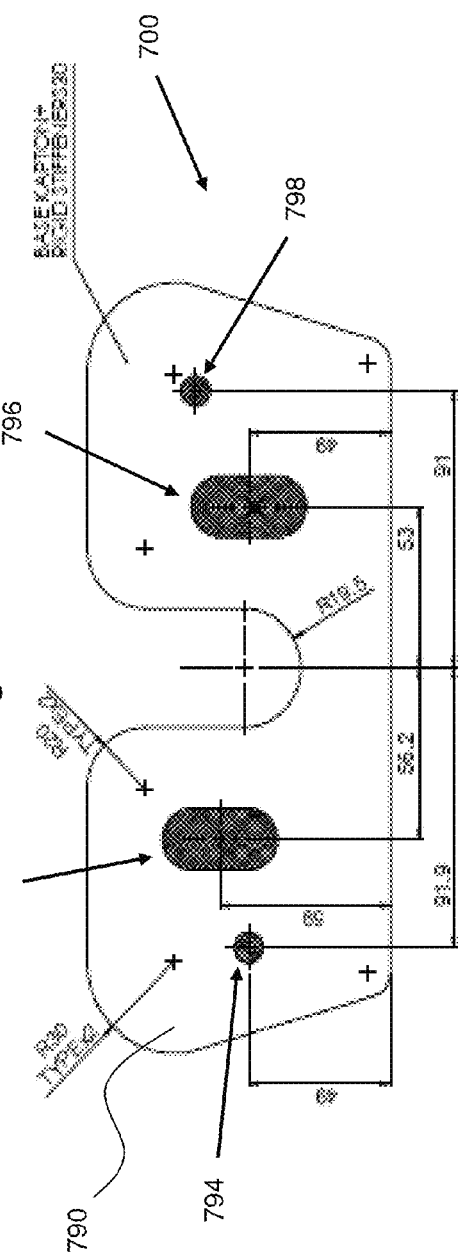
Fig. 7B
Fig. 7C

WEARABLE ANTENNA ASSEMBLY FOR AN IN-VIVO DEVICE

FIELD OF THE INVENTION

The present invention generally relates to an in-vivo sensing system and more specifically to a wearable antenna assembly that facilitates an improved wireless communication between a swallowed in-vivo device and an extra-body receiver or data recorder.

BACKGROUND

In-vivo measuring systems are known in the art. Some autonomous capsule like in-vivo devices, which traverse the gastrointestinal (GI) system, may include an imaging sensor, or imager, for imaging (e.g., capturing images or taking pictures of) the interior of the GI system. An in-vivo device may include one or more imagers and/or sensors of other types (e.g., pH sensor, pressure sensor, temperature sensor, etc.), and/or various types of tools (e.g., micro electro-mechanical system, or "MEMS"), for example to perform surgical operations in vivo and/or to administer medication in the GI system, for example from a container contained in an in-vivo device.

While in operation (e.g., after swallowing), an in-vivo device may wirelessly exchange data with an external (extra-body) receiver. For example, the in-vivo device may wirelessly transmit data (e.g., sensory data; e.g., image data pertaining to captured images) to the external receiver, and the external receiver may wirelessly transmit instructions back to the in-vivo device, for example instructions which depend on data transmitted from the in-vivo device. For example, the in-vivo device may transmit image frames to the receiver, and the receiver may transmit an instruction to the in-vivo device, for example, to change the images' capturing rate, for example, based on captured images.

The length and anatomically-inhomogeneous nature of the GI system—it is about five meters long and it has anatomically distinct sections such as the small intestine and the large intestine—and the way in which the GI tract is situated within the body tends to detrimentally affect wireless communication between the in-vivo device and the external receiver when the in-vivo device reaches certain locations within the GI tract. This detrimental effect, in part, results from the relatively low transmission power that an autonomous, self-contained, in-vivo device uses, and also because body tissues (e.g., muscle tissues, tissues of the GI organs, bone tissue, etc.) interfere with the communication. A poor communication channel may result in noisy communication and even in loss of data (e.g., image data). For example, the in-vivo device may transmit an image but, in a poor communication environment, the receiver might not receive the image.

The communication problem described above is further exacerbated by the massive bone structure of the pelvis that supports the GI organs (e.g., the small intestine, the large intestine) and is even less pervious to radio waves than the soft body tissues. Heretofore, antennas setups/layouts have been designed to enable fairly good communication, between a swallowed in-vivo device and an external receiver, when the in-vivo device is in the upper section/part of the GI system, and, therefore, the effect of the pelvic bones on the quality of communication is relatively low, negligible, or non-existent. U.S. Pat. No. 5,604,531, filed Jan. 17, 1995, entitled "IN VIVO VIDEO CAMERA SYSTEM", U.S. Pat. No. 7,618,366, filed Mar. 8, 2005, entitled "ARRAY SYSTEM AND METHOD FOR LOCATING AN IN VIVO SIGNAL SOURCE", and U.S. Pat. No. 7,650,180, PCT application filed Jul. 4, 2004, entitled "IMAGING SENSOR ARRAY AND DEVICE AND METHOD FOR USE THEREOF" show typical conventional antenna setups. However, the detrimental effect of the pelvis bones on the communication's quality is by far noticeable when the in-vivo device is in the lower section/part of the GI system, where the pelvis bones have the strongest detrimental effect on the communication quality, and the conventional antenna setups used for the communication have been found to be far from optimal, or unsuitable, for sensing signals that originate from a signal source residing in the pelvis.

Since the lower section of the GI tract in general, and the lower part of the colon in particular, is of special clinical interest because of its susceptibility to diseases, it would be beneficial to have an antenna setup that improves wireless communication between the in-vivo device and the external receiver while the in-vivo device traverses the lower section/part of the GI tract, and in every area of the GI tract.

Conventional antenna arrays include antenna elements that are planar 'loop' antennas. One problem with planar 'loop' antennas is that these antennas are directional and they have a relatively sharp null, and, in general, such antennas have a radiation pattern that is similar to a radiation pattern of a dipole antenna. Being directional and having a sharp null, the communication between a swallowed in-vivo device and an antenna element is susceptible to the location of the in-vivo device within the GI system. If one antenna element receives a relatively weak signal, other antennas of the antenna array may receive a stronger signal but, still, there might be situations where all the antennas receive weak signals due to their unsuitable communication characteristics.

While moving an in-vivo device through the GI system is beneficial, there are some drawbacks associated with conventional antennas that are used to exchange data between the in-vivo device and an external receiver. It would be beneficial to have an extra-body antenna setup that enables receiving signals from the in-vivo device regardless of the location of the device in the GI system/tract.

It would, therefore, be beneficial to be able to provide wearable antenna assembly that would improve communication between a swallowed in-vivo device and an extra-body receiver.

SUMMARY OF THE INVENTION

A wearable antenna assembly is provided, which facilitates an improved communication with a swallowable in-vivo device. The wearable antenna assembly may include a posterior antenna assembly that may be accommodated by a posterior pouch, an anterior antenna assembly that may be accommodated by an anterior pouch, and a belt to which the pouches may be fastened.

The posterior antenna assembly may include a flat posterior antenna element that may include a flat, electrically insulating, posterior base. The posterior base may include a lateral portion having a lateral line, and at least a first protrusion that continues from the lateral portion and extends away from the lateral line.

A first antenna element may be formed (e.g., mounted on, laminated on or in, or built into, or by using a printed circuit board ("PCB") technique) in the first protrusion, and the at least first protrusion may be configured, and the first antenna element may be formed therein (e.g., be being mounted on, laminated on or in, or built into, or by using a printed circuit board technique), such that, when the belt is worn by an individual, the first protrusion conveniently lies on, and generally adapted to the shape of the buttocks, such the first antenna element is situated adjacent to or in front of a first of the two greater sciatic notches of the pelvis. The posterior base may include a second protrusion, on which a second antenna element may be formed. The second protrusion may also continue the lateral portion and extend away from the lateral line in the same direction as the first protrusion. The posterior base, with only one protrusion that extends away from the lateral portion, may be "r"-shaped, and with the two protrusions extending away from the lateral portion it may be "U"-shaped. The second protrusion may be configured, and the second antenna element may be formed therein, such that, when the belt is worn by an individual, the second protrusion conveniently lies on, and generally adapted to the shape of the buttocks, such that the second antenna element is situated adjacent to or in front of the second/other greater sciatic notch of the pelvis.

Each of the antenna elements formed in the posterior base may have an orientation that may be defined with respect to the lateral line, and the orientations of the antenna elements may be optimized to maximize signal reception.

The anterior antenna assembly may include a flat, electrically insulating, anterior lateral base having a lateral line, and n antenna elements that may be formed, for example side-by-side, in the anterior lateral base along the lateral line. Each of the n antenna elements may have an orientation according to an orientation setup, that may be defined with respect to the lateral line, and the orientations of the n antenna elements may be optimized to maximize signal reception. The anterior lateral base may be configured, and the n antenna elements may be formed therein, such that, when the belt is worn, the n antenna elements are situated adjacent to, or in front of, the abdomen and maximize signal reception therethrough.

BRIEF DESCRIPTION OF THE DRAWINGS

Various exemplary embodiments are illustrated in the accompanying figures with the intent that these examples not be restrictive. It will be appreciated that for simplicity and clarity of the illustration, elements shown in the figures referenced below are not necessarily drawn to scale. Also, where considered appropriate, reference numerals may be repeated among the figures to indicate like, corresponding or analogous elements. Of the accompanying figures:

FIG. 4A schematically illustrates a wearable antenna assembly position relative to the lateral view of the pelvis according to an example embodiment;

FIG. 4B shows the wearable antenna assembly of FIG. 4A positioned on a human body according to an exemplary embodiment;

FIGS. 7A, 7B and 7C show a posterior antenna element according to an exemplary embodiment;

DETAILED DESCRIPTION OF THE INVENTION

Figure 1:
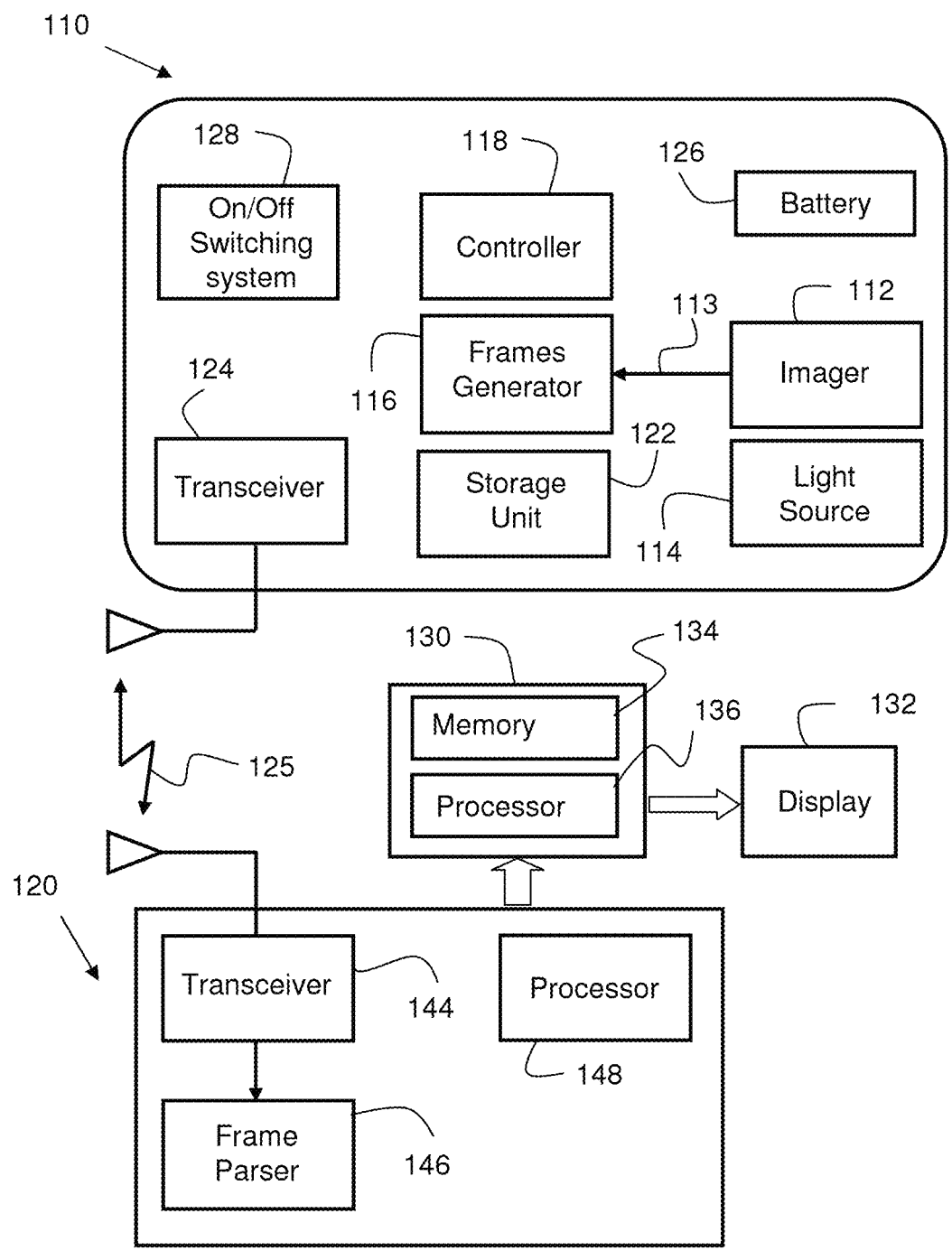
FIG. 1 is a block/schematic diagram of an in-vivo imaging system according to an exemplary embodiment.

The description that follows provides various details of exemplary embodiments. However, this description is not intended to limit the scope of the claims but instead to explain various principles of the invention and the manner of practicing it.

In an adult male human, the GI tract is 5 meters long in a live subject, or up to 9 meters without the effect of muscle tone, and consists of the upper GI tract and the lower GI tract. The GI tract may also be divided into foregut, midgut, and hindgut. The upper GI tract generally includes the esophagus, stomach, and duodenum. With respect to the GI system the exact demarcation between "upper" and "lower" can vary according to the used convention. The lower GI tract includes most of the small intestine and all of the large intestine.

When an in-vivo device traverses the GI system, it may move through the lower GI tract passively or controllably. The lower GI tract, which includes most of the small intestine and all of the large intestine, is the nearest GI part to the pelvis bones and, as explained above, some conventional antenna setups are unable to maintain a good and stable communication channel between the in-vivo device and the external receiver with which the in-vivo device operates when the in-vivo device reaches the lower GI tract. A new wearable antenna assembly that mitigates the communication problems discussed herein is shown in the drawings and described below. In general, the new wearable antenna assembly includes a posterior antenna assembly and an anterior antenna assembly, each of which includes new antenna elements that are arranged, per assembly, in a unique way. Regarding the posterior antenna assembly, its antenna elements may be positioned in a location that optimizes signal reception.

FIG. 1 is a block/schematic diagram of an in-vivo imaging system according to an example embodiment. The in-vivo imaging system may include an in-vivo imaging device 110, external (extra-body) receiver 120 that may function as a data recorder, workstation 130 (e.g., personal computer), and a display 132. In-vivo imaging device 110 may be, for example a swallowable device, capturing images and transmitting corresponding image frames to an external receiving apparatus, such as receiver 120. The image frames may be presented in real-time or after processing, be combined into an image stream or video movie for display to a user, for example by using display 132.

An in-vivo imaging device may have one or more imagers. By way of example, imaging device 110 include one imager; e.g., imager 112 (more than one or two imagers may be used). In-vivo imaging device 110 may also include a light/illumination source 114, a data (e.g., image data or) frame generator 116, a controller 118, a storage unit 122, a transceiver 124, and a power source 126 for powering them. Controller 118, among other things, may controllably operate illumination source 114 to illuminate areas traversed by in-vivo device 110, and coordinates the images capturing timing of imager 112. Controller 118 may temporarily store captured images and related image frames in storage unit 122. Controller 118 may also perform various calculations and store calculation results in storage unit 122.

Frames generator 116 may receive image data 113 from imager 112 and use the image data to produce an image frame ("frame" for short) for the pertinent captured image. A frame typically includes a header field that contains information and/or metadata related to the frame itself (e.g., information identifying the frame, the serial number of the frame, the time the frame, the bit-wise length of the frame, etc.). A frame may also include an uncompressed version of the image data and/or a compressed version thereof, and a decimated image. The header may also include additional information, for example a readout of any additional sensor integrated into device 110. Controller 118 may operate illumination source 114 to illuminate, for example, four times per second to enable capturing four images per second, and transceiver 124 to concurrently transmit corresponding frames at the same rate or at a different rate. Controller 118 may operate illumination source 114 to capture more images per second, for example seventeen images or more than seventeen images per second, and transceiver 124 to concurrently transmit corresponding frames at the same rate.

After frames generator 116 produces a frame for a currently captured image, controller 118 wirelessly communicates 125 the frame to data recorder 120 by using transceiver 124. Receiver 120 may be a stand alone receiver that is located close enough to the person swallowing the in-vivo device in order to facilitate receiving and processing of the transmitted frames by data recorder 120. However, as explained above, the quality of the communication between the in-vivo device and the external receiver strongly depends on the location and orientation of the in-vivo device in the GI tract: in some locations of the in-vivo device the signal-to-noise ratio ("SNR") may be much lower than in other locations, which may result in loss of images if the SNR gets too low.

Data recorder 120 may include a transceiver 144, a frame parser 146, and a processor 148 for managing transceiver 144 and frame parser 146. Data recorder 120 may include additional components (e.g., USB interface, Secure Digital ("SD") card driver/interface, controllers, etc.), elements or units, for example, for communicating with (e.g., transferring frames, data, etc. to) an external processing/displaying system that may be configured to process images captured by in-vivo device 110.

In one embodiment transceiver 144 receives a frame corresponding to a particular captured image, and frame parser 146 parses the frame to extract the various data entities contained therein (e.g., image data, decimated image associated with, or representing the particular captured image, etc.).

The in-vivo imaging system of FIG. 1 may include a workstation 130. Workstation 130 may include a display or be functionally connected to one or more external displays, for example to display 132. Workstation 130 may receive image frames, and other types of data from data recorder 120, and present them in real-time, for example as live video, or produce a video stream. Workstation 130 may include a memory, such as memory 134, for storing the frames (and possibly data of other types) transferred from data recorder 120, and a processor, such as processor 136, for processing the stored data (e.g., image data). In-vivo imaging device 110 may also include an "on/off" switching system 128 for switching imaging device 110 on and off.

Signals that are transmitted from in-vivo device 110 (e.g., by transceiver 124) are received by antennas that are attached or laid in proximity to the body of the person swallowing the in-vivo device. The signals received by the antennas are forwarded to data recorder 120, for analysis and interpretation, via a communication cable. (The antennas and the communication cable are not shown in FIG. 1.)

Components of the system and device according to embodiments of the present invention may be similar to components used in a capsule endoscopy system commercially available from the common assignee of the present invention, which capsule endoscopy system is commercially known as the PillCam® capsule.

Figures 2A, 2B:
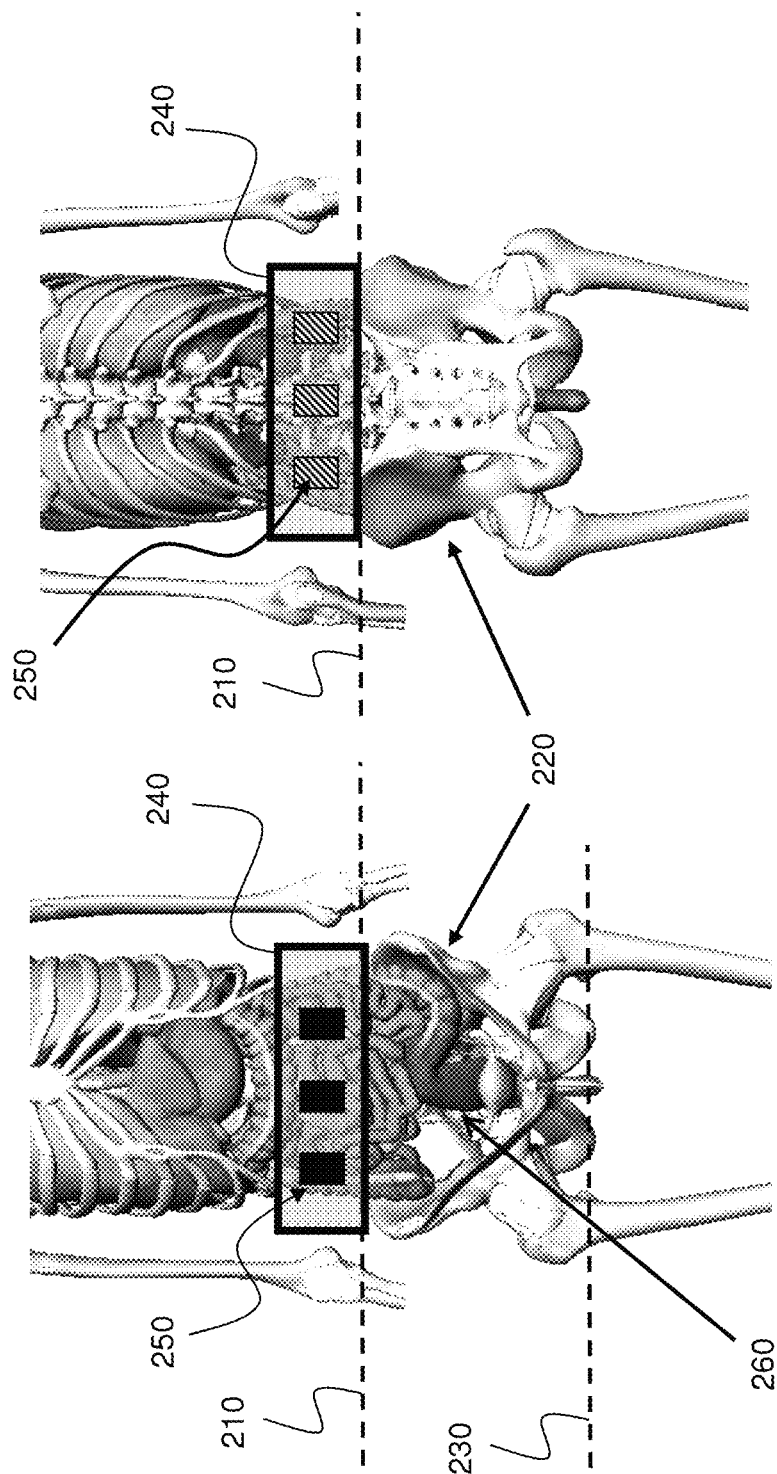
FIGS. 2A and 2B respectively depict the anterior view and the posterior view of a human skeleton, including the position of the GI system therein.

FIGS. 2A and 2B respectively depict the anterior view and the posterior view of a human skeleton, including the position of the GI system therein. The GI system may be roughly divided into two sections with respect to a bisection line 210 ('pelvis line'): a lower section that includes the GI organs below line 210, and an upper section that includes the GI system organs above line 210. The terms "lower" and "upper" in the present context are intended to suggest only the relative positions of the various GI organs with respect to an upright person. Pelvis 220 is shown between line 210 and line 230. Pelvis 220 contains and supports the lower section of the GI system that typically includes part of the small intestine and the entire or most of the large intestine As explained above, conventional antenna layouts are not optimized to the structure of the pelvis. For example conventional antenna layouts disregard the bone structure of the pelvis and the signal attenuation caused by it when the in-vivo device reaches, or moves through, the lower part of the GI tract. For example, some conventional antennas, which receive signals from swallowed in-vivo devices, are placed just above the ilium crest, as shown at 240 in FIG. 2A (antenna belt 240 may include one or more antenna elements similar to antenna element 250, which is shown in simplistic form). While antenna belt 240 (and other antenna layouts in which antenna elements are positioned above the ilium crest, may provide a relatively good reception coverage for signals that are transmitted from the upper GI system (the part of the GI system above bisection 210), it may provide a non-stable to poor reception coverage for signals that are transmitted from some regions of the GI part below bisection line 210.

The GI area referred to by numeral reference 260 has been found to be one of the more problematic areas in terms of radio communication, due to the pelvis bones that communication-wise mask these areas. The aforesaid communication problem is mitigated by taking advantage of specific openings in the pelvis, which are shown in FIGS. 3A, 3B and 3C, which are described below, through which radio signals can relatively easily pass ('easily': without being attenuated by a bony medium), and situating antenna elements in front of, or in proximity to, these openings, as demonstrated by FIG. 4.

Figures 3A, 3B:
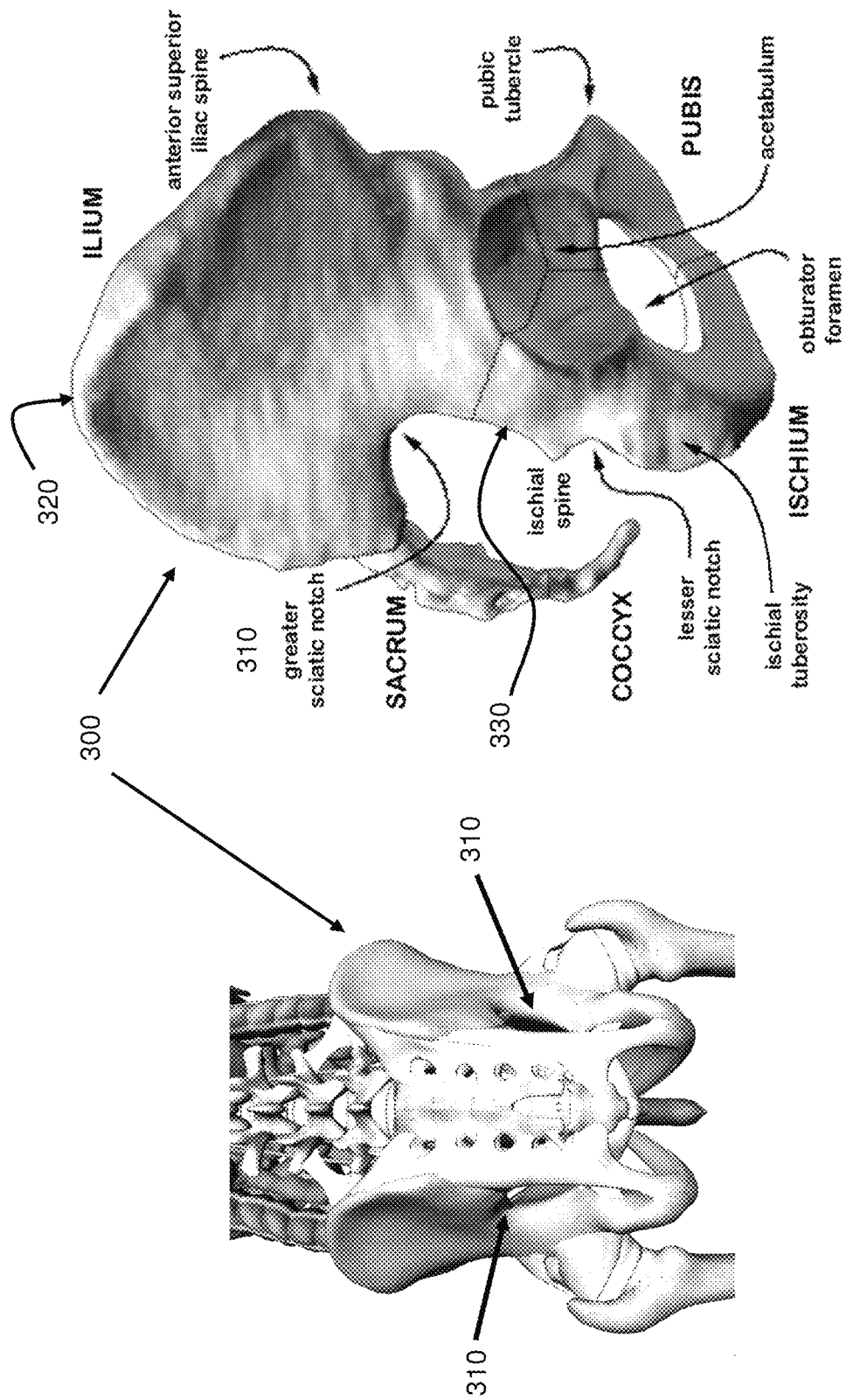
FIGS. 3A, 3B and 3C respectively depict the posterior view, the lateral view and the anterior view of the pelvis.
Figure 3C:
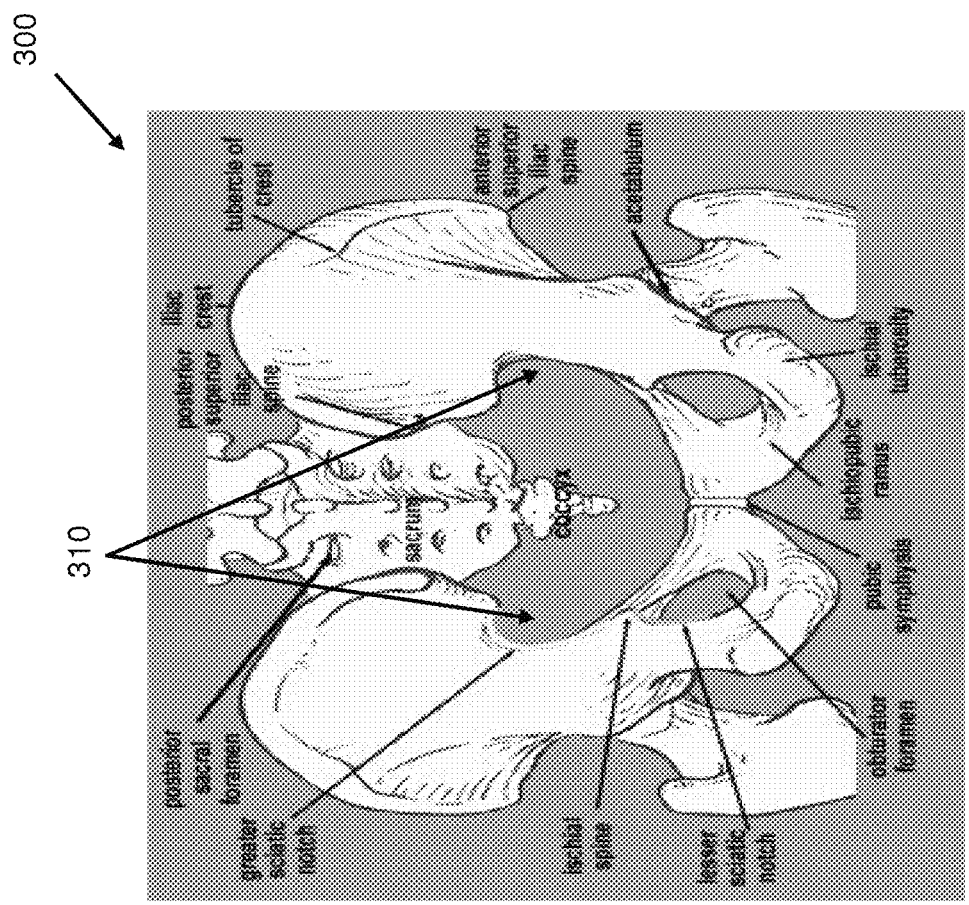

FIG. 3A depicts an example pelvis 300 with two openings 310. Each of openings 310 generally has a shape of a notch that is known in the field of osteology as a "greater sciatic notch". Different perspectives of the greater sciatic notches are shown in FIGS. 3B and 3C, at 310. Each greater sciatic notch is formed by the ilium bone (a bone that is shown in FIG. 3B at 320) and the ischium bone (a bone that is shown in FIG. 3B at 330).

The signal transmitted by the in-vivo device is generally isotropic. Therefore, when an in-vivo device reaches the lower section of the GI system, at least a portion of the radio signal that the in-vivo device transmits passes through greater sciatic notches 310, for which reason this signal portion is significantly less attenuated comparing to other signal portions that pass through the pelvis bones. Signals that pass through the greater sciatic notches are still attenuated by soft tissues, but this kind of attenuation is tolerable as it still results in significantly better signal reception compared to conventional positioning of antennas. That is, antennas situated near, or in front of, greater sciatic notches 310 receive significantly stronger signals from the lower part of the GI system comparing to antennas that are situated traditionally, for example in the way shown in FIGS. 2A-2B (e.g., antenna belt 240).

FIG. 4A shows a lateral view of a skeleton 400 and an example wearable antenna assembly 410 positioned thereon according to an example embodiment. Antenna layout 410 may include an anterior/frontal antenna 420 and a posterior antenna 430. By "anterior antenna" is meant an antenna that is (to be) situated at, or adjacent to, the abdomen. By "posterior antenna" is meant an antenna that is (to be) situated at, or adjacent to, the back.

Figure 7A:
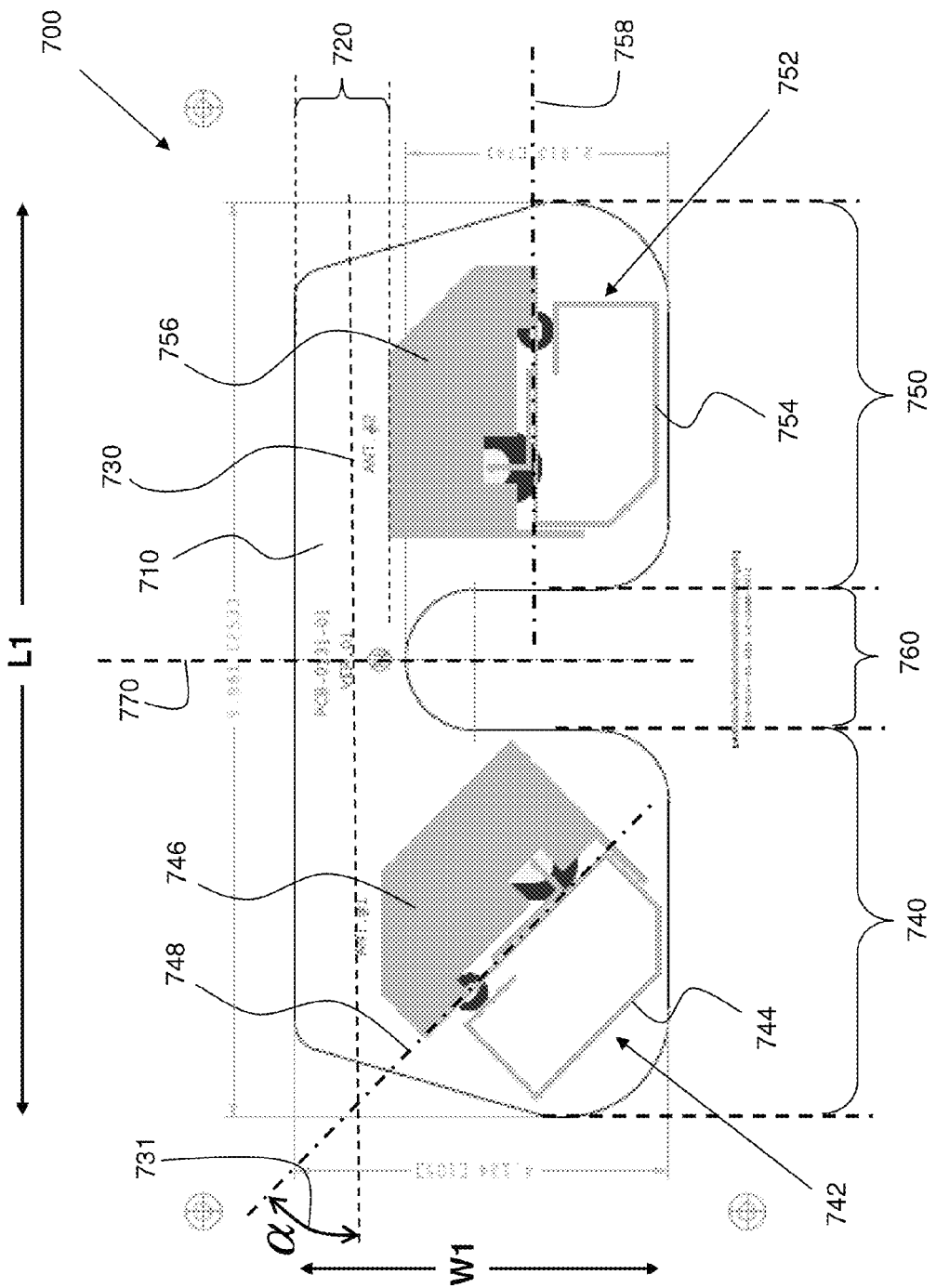
Figure 8:
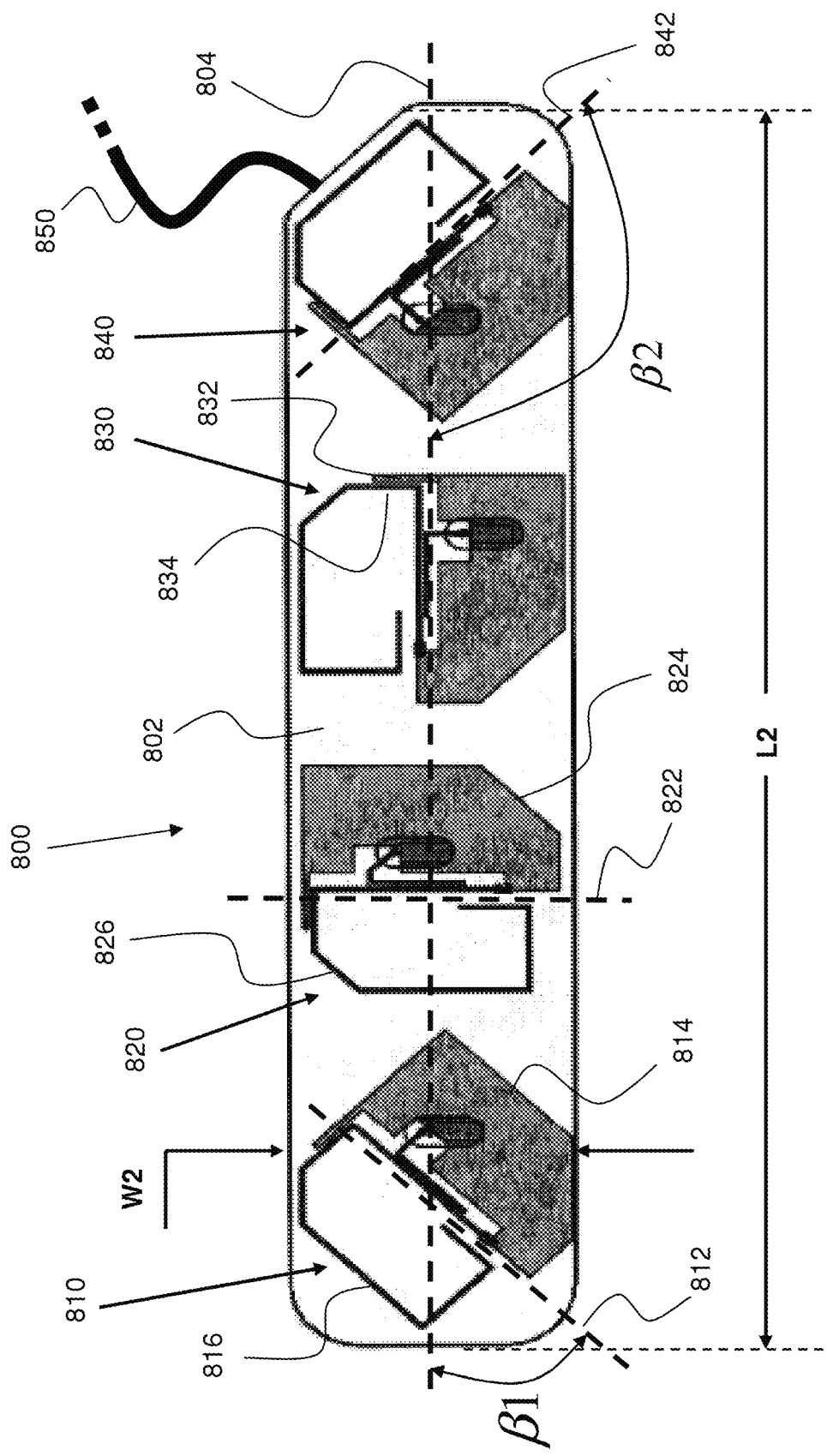
FIG. 8 depicts an anterior antenna assembly according to an example embodiment.

According to the present invention the anterior antenna and the posterior antenna may each include one or more antenna elements. An example anterior antenna is shown in FIG. 8 and an example posterior antenna in shown, for example, in FIG. 7A. (FIG. 7A and FIG. 8 are described below.) Referring again to FIG. 4A, posterior antenna 430 is situated on the buttocks, adjacent to, or in proximity to, the greater sciatic notches (a greater sciatic notche is pointed at by an arrow 440) in order to optimize reception of signals that are transmitted from an in-vivo device (e.g., from in-vivo device 110) that is located in the lower part of the GI tract. Optimal reception from the lower part of the GI tract is obtained because the signal, which the in-vivo device transmits, passes through the greater sciatic notches with significantly reduced attenuation.

When the in-vivo device transmits a signal while it is in the upper part of the GI system (e.g., above line 210), the signal picked up by posterior antenna 430 is relatively weak, or non-existent, due to the adverse effect of the pelvic bones. However, anterior antenna 420 typically receives a much stronger signal because, unlike the lower part of the GI tract, the abdomen does not include bones, nor it is protected or shielded by bones that, as explained above, attenuate radio signals. When the in-vivo device transmits a signal while it is in the lower part of the GI system (e.g., below line 210), the signal picked up by anterior antenna 420 may be weak, or non-existent, but posterior antenna 430 may receive a much stronger signal because it is located in proximity to the greater sciatic notches. Using an antenna layout that includes an anterior antenna (e.g., anterior antenna 420) and a posterior antenna (e.g., posterior antenna 430) that is adapted to optimize reception of signals that pass through the greater sciatic notches, ensures that a stronger signal is obtained from the in-vivo device regardless of whether the in-vivo device is in the upper part of the GI system, or in the lower part thereof.

Figure 4C:
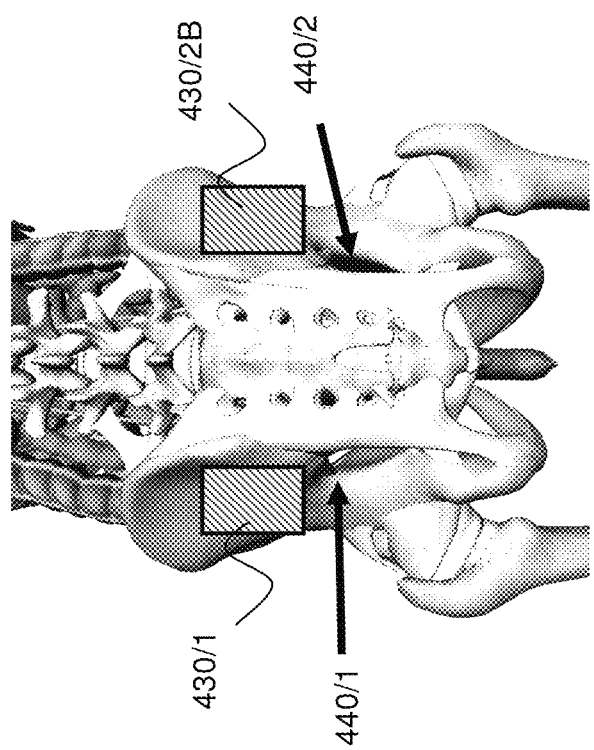
FIG. 4C schematically illustrates a posterior antenna assembly position relative to the posterior view of the pelvis according to an exemplary embodiment.

FIG. 4B shows wearable antenna assembly 410 of FIG. 4A positioned on a human body. With respect to FIGS. 4A-4B, like reference numerals designate, or refer to, like elements/objects. Posterior antenna assembly 430 may be positioned on the upper portion of buttocks 450, as demonstrated by FIG. 4B, in order to minimize inconveniency to the person who wears it. FIG. 4C schematically illustrates the position of posterior antenna setup 430 of FIGS. 4A-4B relative to the posterior view of the pelvis according to an example embodiment. In order to improve radio communication when the in-vivo device is inside the pelvis, posterior antenna 430/1 is positioned on the buttocks adjacent to, or in proximity to, greater sciatic notch 440/1, and posterior antenna 430/2 is positioned on the buttocks adjacent to, or in proximity to, greater sciatic notch 440/2.

Traditionally, antenna elements are adhered to various points on patients (e.g., on the abdomen, on the rib cage, etc.), the reason being that, having to be carried by/on patients, the antenna elements have to be small and light, and, as such, they have to be as close to the body as possible in order to be able to receive signals with an acceptable strength. An array of antennas with individual antenna elements separately adhered to the patient body may also be easily adjusted to the dimensions of each individual patient. In another configuration, the traditional antenna elements are incorporated into a wearable belt or vest, which incorporation may result in inferior signal reception due to distancing of the antenna elements from the patient body. In accordance with the present invention, the geometry of the antenna elements and the wearable antenna assembly overcome some of the drawbacks of some conventional antenna setups. A widely used conventional antenna geometry is shown in FIGS. 5A and 5B, which are described below, and an example antenna element geometry according to an example embodiment is shown, for example, in FIG. 6.

Figure 5B:
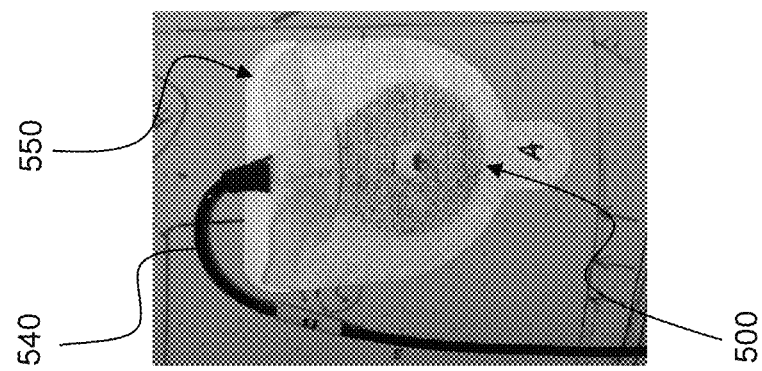
FIGS. 5A and 5B depict a conventional, prior art antenna element for sensing in-vivo signals.
Figure 5A:
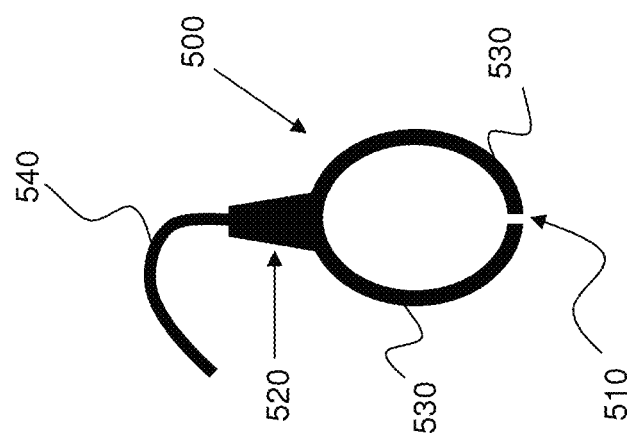

FIGS. 5A and 5B show a traditional antenna 500, which is known in the field of antennas as a "halo antenna". Referring to FIG. 5A, antenna 500 is a horizontally polarized, omni-directional ½ wavelength dipole antenna. It is shaped like a loop with a small break, or discontinuity, 510 on the side of the loop directly opposite the feed point 520, so that the dipole ends do not meet. The antenna is usually one continuous conductor 530. Being horizontally polarized, halo antennas have very little vertical polarization components, and, in general, they perform poorly for vertically polarized signals.

Due to their electrical characteristics (e.g., polarization), antenna 500 (and like antennas) has to touch the body's skin, or at least has to be not more than a few millimeters away from the body's skin, in order to be able to receive signals with acceptable strength. The reason for this requirement is that the combination of the body's electrical characteristics and a loop antenna, when they are in close proximity, form an electrical circuit that enables the antenna to resonate in response to radio frequency ("RF") signals, which may have, for example, a 30-MHz bandwidth centered, for example, at 434 MHz. The stronger the resonance, the stronger the antenna's signal (the better the reception). Distancing the antenna away from the body (e.g., more than 2-3 millimeters away) significantly detracts from this capability, up to a point where the signal to noise ratio ("SNR") at the receiver gets so low that communication may be disconnected. Antenna element 500 typically has a gain of 1 decibel relative to an isotropic antenna and an impedance of 70-80 ohms when the distance between the antenna element and the body is less than 3-4 millimeters. When antenna element 500 is distanced farther away from the body (e.g., more than 3-4 millimeters), its performance is significantly degraded. Cable 540 connects antenna 500 to a receiver, for example to a data recorder such as data recorder 120. Referring to FIG. 5B, antenna 500 is shown embedded in a pocket 550 that is attachable to the skin, for example by glue. As explained above, attaching pockets such as pocket 550, or the antennas themselves, to the skin causes discomfort to the person wearing the antennas.

Figure 6:
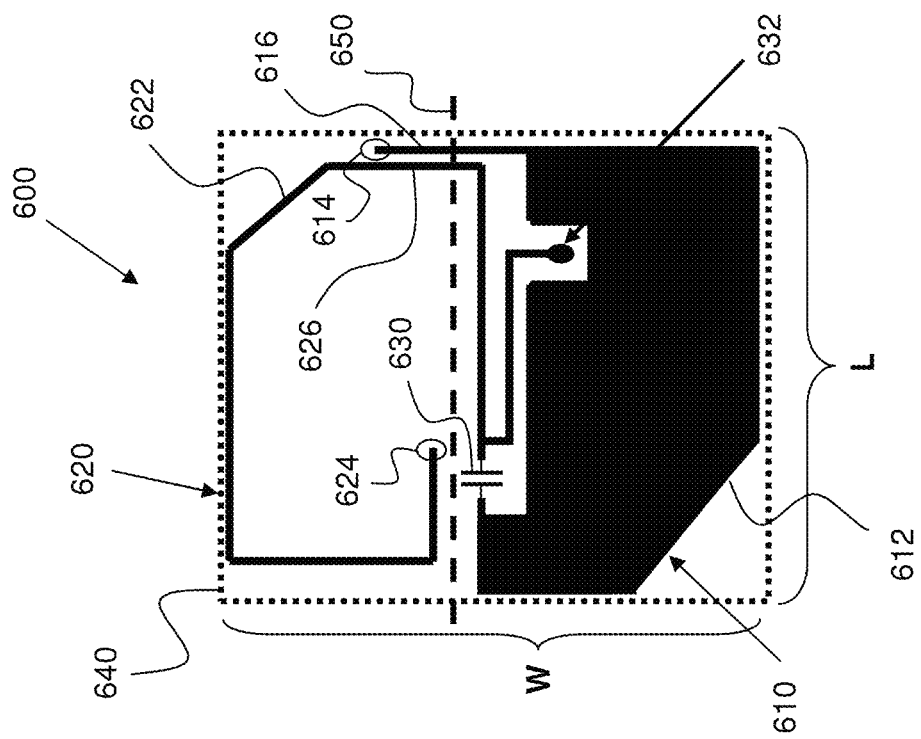
FIG. 6 depicts an antenna element for sensing in-vivo signals according to an exemplary embodiment.

FIG. 6 shows an antenna element 600 according to an example embodiment. Antenna element 600 includes a ground plane 610 and a conducting strip 620. Each of ground plane 610 and conducting strip 620 has a truncation: ground plane 610 has a truncation 612, and conducting strip 620 has a truncation 622. Truncation 612 is generally situated opposite truncation 622 (truncations 612 and 622 are located at opposite sides/vertices of antenna element 600). In some embodiments, only one element (e.g., the ground plane or the conducting strip) may have a truncation. In other embodiments neither the ground plane nor the conducting strip has a truncation. Ground plane 610 and conducting strip 620 are isolated from one another, in terms of direct current ("DC"), by capacitor 630, which is used also for RF tuning. That is, capacitor 630 and the inductance, L, of the antenna make up an electrical circuit that resonates in response to radio signals. Output terminal 632 outputs the radio signal received at the antenna element, in order for it to be provided to a radio receiver for deciphering/interpretation.

Ground plane 610 and conducting strip 620 are formed on a common flat substrate, side-by-side, for example by using PCB techniques. Ground plane 610 may have a segment (the segment is shown at 616) that is parallel to, and partly overlaps, a segment of conducting strip 620 (the segment of conducting strip 620 is shown at 626). Segment 626 may be connected to truncation 622 of conducting strip 620.

Antenna element 600 is a type of a folded dipole antenna. In a 'typical' folded dipole antenna the tips of the antenna are 'folded back' until the two tips almost meet at the feed point, such that the antenna comprises an entire wavelength. A folded dipole antenna, therefore, has a greater bandwidth than a standard half-wave dipole. Referring to FIG. 6, antenna 600 has two tips, or ends (the tips, or ends, are shown at 614 and 624). Since tip/end 624 is folded back while tip/end 614 extends out from ground plane 610, antenna 600 may be thought of as being an "asymmetric folded dipole antenna".

Antenna element 600 is generally rectangularly shaped (it may be circumscribed by a rectangle 640). Antenna 600 has an orientation that may be defined, or expressed, for example, by an orientation line 650. As shown, for example in FIG. 7A and FIG. 8, a wearable antenna assembly may include a plurality of antenna elements that may be identical or similar to antenna element 600, and each antenna element may have a different orientation than the adjacent antenna elements. Orientation line 650 is shown slightly off-centered for clarity. The length, L, of rectangular antenna 600 may be 100 millimeters or about 100 millimeters (e.g., L=100±15 millimeters). The width, W, of rectangular antenna 600 may be 80 millimeters or about 80 millimeters (e.g., W=80±10 millimeters). Antenna 600 may have other lengths and/or widths.

Due to its design, antennas identical or similar to antenna 600 do not have to be as closed to the skin as antenna 500; they can be distanced away from the skin (e.g., up to 30 centimeters), and yet they facilitate better radio communication (in comparison to antenna 500 or similar antennas) in the RF range mentioned above (e.g., a 30-MHz bandwidth centered, for example, at 434 MHz).

An antenna element such as antenna element 600 typically has a gain of 2 decibels relative to an isotropic antenna and an impedance of 70-80 ohms for an extended range relative to antenna element 500. That is, antenna element 600 may be distanced up to 30 centimeters away from the body and still maintain these electrical characteristics.

FIG. 7A shows a posterior antenna element 700 for receiving radio signals that originate from a swallowed in-vivo device and pass through the two greater sciatic notches of the pelvis. Posterior antenna element 700 may include a posterior flat antenna base 710, or posterior base 710 for short. Posterior antenna element 700 may be one of two or more antenna assemblies that may be attached to a belt to make up a wearable antenna assembly. Another antenna assembly, which is referred to herein as the "anterior antenna assembly", is shown in FIG. 8, which is described below.

Posterior base 710 may generally be an oblong shaped object, having a length L1 and width W1. Posterior base 710 may include a lateral portion 720 having a lateral line 730, and at least a first protrusion 740 that may continue from (it may be an extension of) lateral portion 720 and extends away from lateral line 730, typically perpendicularly with respect to lateral line 730. The term "typically perpendicularly with respect to lateral line 730" means at a right angle or substantially at a right angle (e.g., 90°±30°) with respect to lateral line 730. For example, first protrusion 740 may extend away at 60 degrees, or at 80 degrees, etc., from lateral line 730. A first antenna element (the first antenna element is shown at 742) may be mounted on, incorporated or embedded in, or built into first protrusion 740. Antenna element 742 may be identical or similar to antenna element 600 of FIG. 6. For example, antenna element 742 may include a conducting strip 744 that may be identical or similar to conducting strip 620 of antenna element 600, and a ground plane 746 that may be identical or similar to ground plane 610 of antenna element 600.

Posterior base 710 may also include a second protrusion 750 that may also continue from (e.g., it may also be an extension of) lateral portion 720, and may also extend away from lateral line 730, typically perpendicularly with respect to lateral line 730. First protrusion 740 and second protrusion 750 of posterior base 710 may be symmetrical with respect to symmetry line 770, but they need not be symmetrical. Symmetry line 770 may be perpendicular to lateral line 730, but it need not be perpendicular lateral line 730.

A second antenna element (the second antenna element is shown at 752) may be mounted on, incorporated or embedded in, or built into second protrusion 750. Each of antenna elements 742 and 752 may be identical or similar to antenna element 600 of FIG. 6. For example, antenna element 752 may include a conducting strip 754 that may be identical or similar to conducting strip 620 of antenna element 600, and a ground plane 756 that may be identical or similar to ground plane 610 of antenna element 600. The ground plane of each antenna element (e.g., ground plane 746, or ground plane 756, or both ground planes) may be situated in-between lateral portion 720 and the pertinent conducting strip.

First protrusion 740, or second protrusion 750, or both protrusions 740 and 750 may be configured (e.g., sized, shaped, produced from materials, etc.) such that, when the belt is worn on the person's waist, posterior antennas element 700 is fitted to its wearer's buttocks such that one antenna element is tightly positioned adjacent to one of the two greater sciatic notches of the pelvis and, if there is also a second antenna element (e.g., on another protrusion of posterior base 710), the second antenna element is tightly positioned adjacent to the other greater sciatic notch. By way of example, the overall length, L1, of posterior base 700 may be 253 millimeters or approximately 253 millimeters, and the overall width, W1, of posterior base 710 may be 105 millimeters or approximately 105 millimeters. The thickness of posterior base 710 may be 13 millimeters, or approximately 13 millimeters. Posterior base 710 may have a gap 760 to make posterior base 710, as a whole, more flexible in multiple direction. For example, gap 760 enables protrusions 740 and 750 to be twisted or flexed to opposite directions with respect to lateral line 730, for example it enables one protrusion (e.g., protrusion 740) to be twisted or flexed towards the viewer and the other protrusion (e.g., protrusion 750) away from the viewer. Gap 760 may enable protrusions 740 and 750 to be twisted or flexed also with respect to symmetry line 770. By imparting to posterior base 710 more flexibility, gap 760 enables posterior base 710 to be better fitted to its wearer. Typically, gap 760 is aligned or coincides with symmetrical line 770, but it need not.

Similar to antenna element 600, each of antenna elements 742 and 752 has a longitudinal axis that is associated with it and defines its orientation, for example, relative to lateral line 730. An "orientation" of an antenna element may be expressed as the direction of its longitudinal axis, or as an angle, $\alpha$, between its longitudinal axis and lateral line 730. For example, antenna element 742 has a longitudinal axis 748 that defines the orientation of antenna element 742 relative to lateral line 730, and antenna element 752 has a longitudinal axis 758 that defines the orientation of antenna element 752 relative to lateral line 730. As shown in FIG. 7A, antenna element 742 (a "first antenna" of posterior base 710) has an orientation (a "first orientation") that differs from the orientation (a "second orientation") of antenna element 752 (a "second antenna" of posterior base 710): the orientation of antenna element 742 is at an acute angle, $\alpha$, with respect to lateral line 730, as shown at 731, and the orientation of antenna element 752 is parallel to lateral line 730 (i.e., $\alpha$=0 degrees). In general, the first orientation may be defined to be $\alpha 1$ (e.g., the angle between antenna element 742 and lateral line 730, where $0 \leq \alpha 1 \leq 90$ degrees), and the second orientation may be defined to be $\alpha 2$ (e.g., the angle between antenna element 752 and lateral line 730, where $0 \leq \alpha 2 \leq 90$ degrees), where $\alpha 1 \neq \alpha 2$ in order to ensure good reception of radio signals that are transmitted from a swallowed in-vivo device no matter the location of the device in the lower part of the GI tract, or its orientation. In the example shown in FIG. 7A, $\alpha 1 \cong 45$ degrees, and $\alpha 2$=0 degrees. In another example, $\alpha 1$ may be 80 degrees and $\alpha 2$ may be 20 degrees. In another example, $\alpha 1$ may be equal to 0 degrees and $\alpha 2$ may be equal to 45 degrees plus/minus 10 degrees. Orientations $\alpha 1$ and $\alpha 2$ may be adjusted, for example as per the person wearing the posterior antenna element 700.

Posterior base 710 may include a flat, flexible and electrically insulating material, such as Kapton. (Kapton is a polyimide film developed by "DuPont". Kapton can remain stable in a wide range of temperatures, and is used in flexible PCBs.) Additionally or alternatively, posterior base 710 may include a flat dielectric substrate of another type. Posterior base 710 may be consisted of one flexible layer, or it may be multilayered, having multiple flexible layers. Posterior base 710 may be flexible with respect to any of lateral line 730 and symmetry line 770, or with respect to both lateral line 730 and symmetry line 770. Posterior base 710 may be flexible with respect to all directions; i.e., it may be isotropically flexible, to enable a better fit of the posterior antenna element 700, as a whole, to the buttocks of its wearer. The flexibility of posterior base 710 may be direction dependent. Posterior base 710 may be consisted of or include any material, or any combination of materials, that facilitates the required flexibility characteristics.

FIG. 7B and FIG. 7C respectively depict an upper side (780 in FIG. 7B) and a bottom side (790 in FIG. 7C) of posterior antenna element 700 of FIG. 7A according to an example embodiment. After an antenna identical or similar to antenna 600 of FIG. 6 (e.g., antenna 742 and 752 of FIG. 7A) is formed in (e.g., mounted on, laminated on or in, or built into) a posterior base such as posterior base 710, capacitor 630 and terminal 632 may malfunction under frequent or vigorous folding/flexing of the posterior base. Therefore, these areas of the posterior base may be stiffened in order to enable them to withstand folding induced stresses and other types of mechanical stresses. Referring to FIG. 7B, posterior base 710 may include rigid stiffeners 782 and 784 for the capacitor and the output terminal of antenna element 742, respectively, and rigid stiffeners 786 and 788 for the capacitor and the output terminal of antenna element 752, respectively. Referring to FIG. 7C, posterior base 710 includes supplemental rigid stiffeners: rigid stiffeners 792 and 794 for the capacitor and the output terminal of antenna element 742, respectively, and rigid stiffeners 796 and 798 for the capacitor and the output terminal of antenna element 752, respectively. The posterior antenna assembly, which may be part of the wearable antennas assembly, may include posterior antenna element 700, and a flat, flexible and electrically insulating, support, as shown, for example, in FIG. 7D and FIG. 7E. It is known that the distance between the two greater sciatic notches and their relative locations in the pelvis do not change significantly from one person to another despite changes in their height, weight, or body mass index ("BMI"). Therefore, a one-size posterior antenna element identical or similar to posterior antenna element 700 may fit all.

Figure 7D:
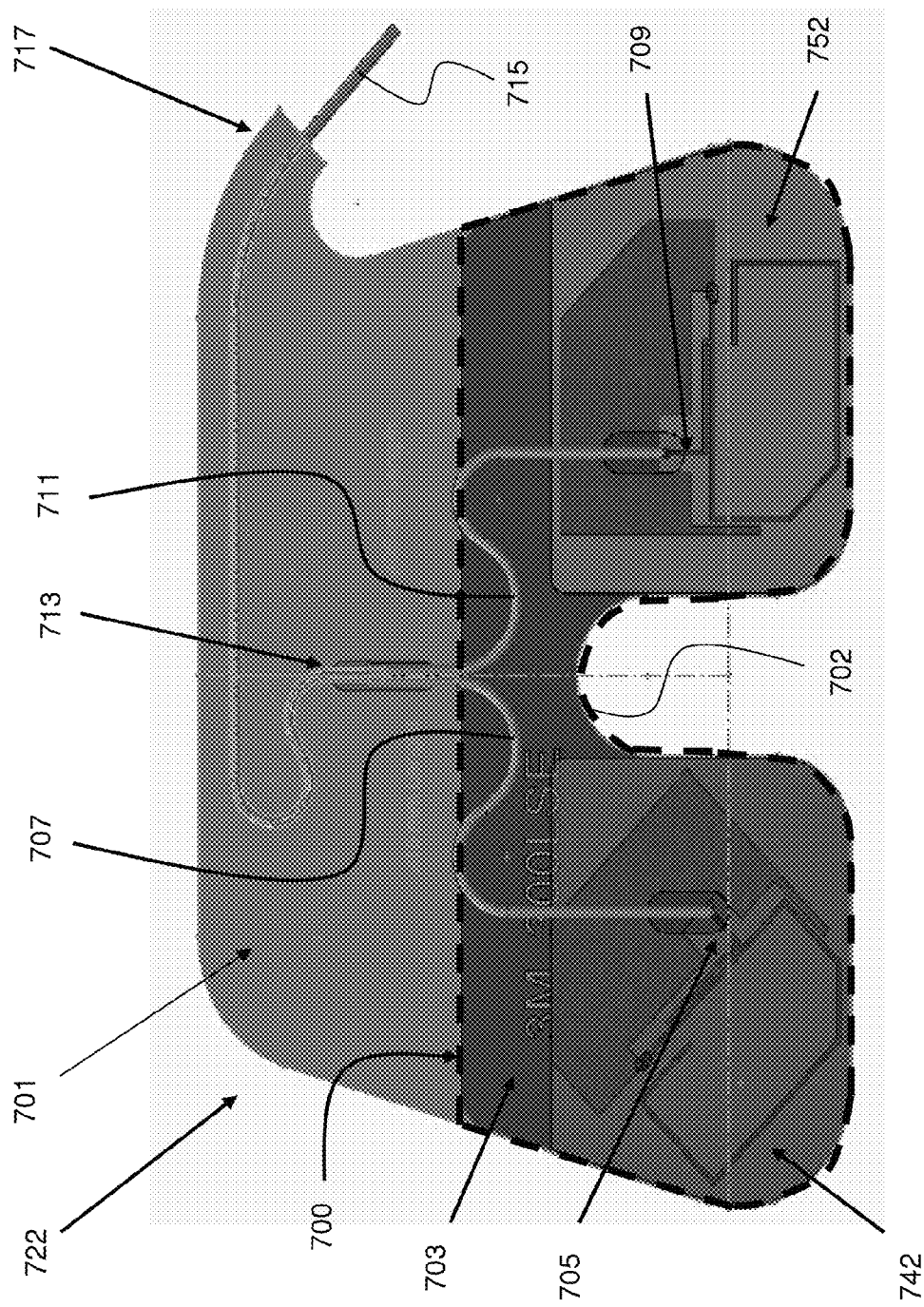
FIGS. 7D and 7E show a posterior antenna assembly according to an exemplary embodiment.

FIG. 7D shows a posterior antenna assembly (a posterior insert) 722 according to an example embodiment. Posterior antenna assembly 722 may include a flat, flexible, posterior support 701 and posterior antenna element 700 that is supported by flat, flexible, posterior support 701. Posterior antenna element 700 may be mounted on flat posterior support 701, for example by using lamination techniques. Posterior antenna element 700 may fully or partly overlap a portion of posterior support 701. In FIG. 7D, posterior antenna element 700 fully overlaps a portion of posterior support 701 (posterior antenna element 700 is shown circumscribed by a dotted line 702).

Posterior support 701 may be produced from an isotropically flexible, electrically insulating, material such as Kapton, onto which posterior antenna element 700 may be mounted (e.g., by using lamination techniques), or it may be produced from a non-isotropically flexible material that may be, or based on, or include, for example, Kapton or similar material. Posterior antenna element 700 may include a base or layer, such as base or layer 703, on which antenna elements 742 and 752 may be formed. The output signal of antenna element 742 (the radio signal received at this antenna) may be provided, via terminal 705, to antenna cable 707. Likewise, the output signal of antenna element 752 (the radio signal received at this antenna) may be provided, via terminal 709, to antenna cable 711. Antenna cables 707 and 711 may be joined, at junction 713, to one signal cable 715 that passes via, or through, a 'neck' 717 of support 701.

Each of the antenna elements 742 and 752 may have an orientation that may be defined with respect to the lateral line of posterior base 703, or with respect to one another, and the orientations of the antenna elements may be optimized to maximize signal reception through the greater sciatic notches. The posterior antenna assembly may further include a posterior pouch (e.g., pouch 912 of FIG. 9, pouch 1100 of FIG. 11) to accommodate posterior antenna element 700 and posterior support 701. The posterior pouch may be releasably connectable or attachable to a belt, for example by using a Velcro fastener.

Figure 7E:
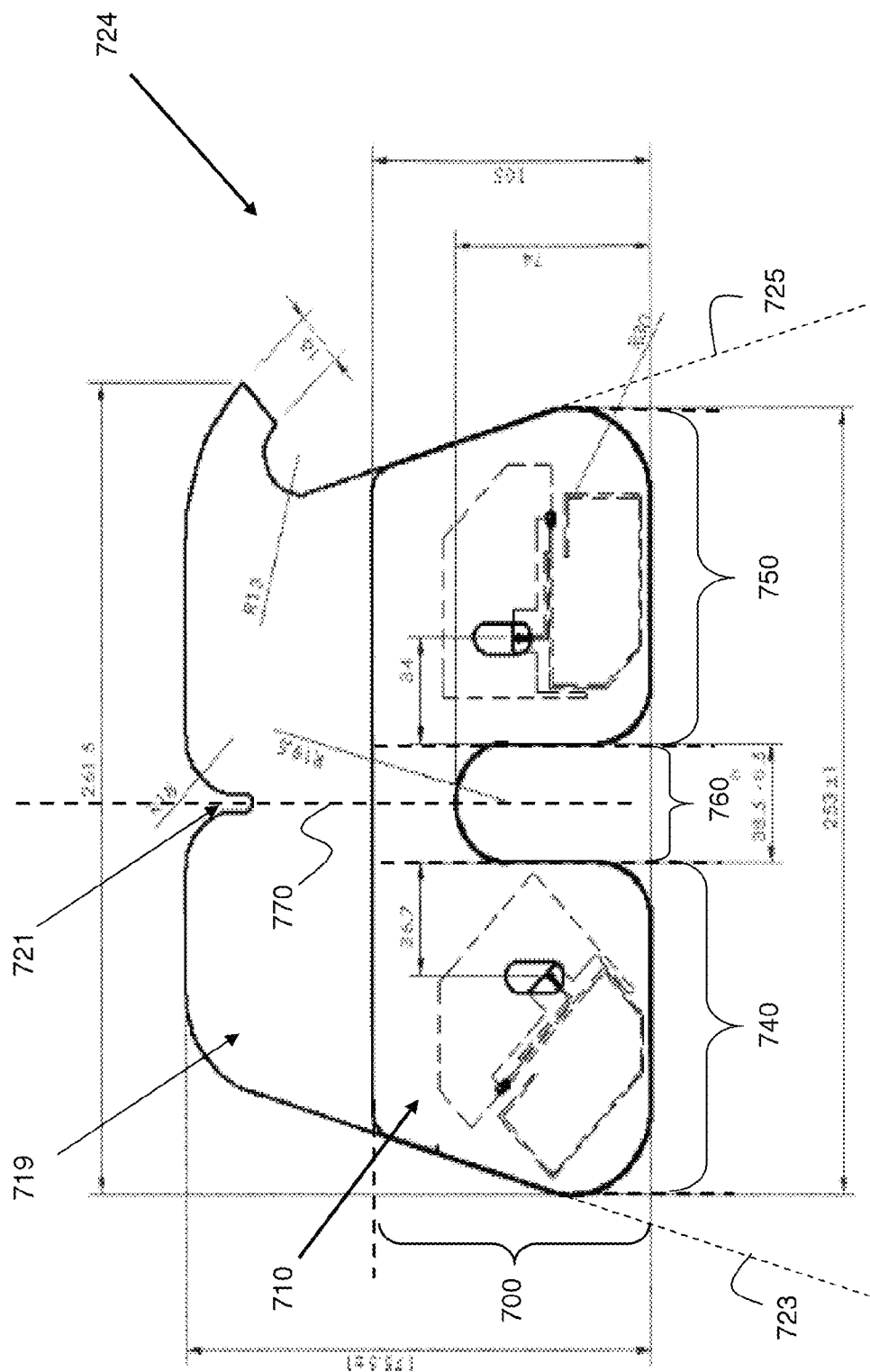

FIG. 7E shows a posterior antenna assembly (a posterior insert) 724 according to another example embodiment. Posterior antenna assembly 724 may include a flat, flexible, support 719, and posterior antenna element 700 that may be mounted on, and supported by, flat support 719. Support 719 may include a notch 721 that is aligned with symmetry line 770 and situated opposite gap 760 that separates between protrusions 740 and 750 of posterior base 710. Support 719 may be produced from a flexible, possibly uniform, electrically insulating material, such as Kapton, onto which posterior antenna element 700 may be mounted. Support 719 may include a notch 721 for rendering posterior antenna assembly 724 more flexible, as a whole, with respect to symmetry line 770. The antenna cables connected to the antenna elements of posterior antenna assembly 724 are not shown in FIG. 7E. Posterior antenna element 700, and posterior antenna assembly 724 in general, has sides 723 and 725, and an angle δ between sides 723 and 725 may be zero (sides 723 and 725 are parallel) or greater than zero. For example, in FIG. 7E δ=32 degrees. The wearable antenna assembly disclosed herein may also include an anterior antenna assembly, as shown in FIGS. 8 through 11, which are described below.

FIG. 8 shows an anterior antenna assembly (an anterior insert) 800 according to an example embodiment. Anterior antenna assembly 800 may be an oblong shaped object, having a length L2 and width W2. Anterior antenna assembly 800 may have other shapes. Anterior antenna assembly 800 may include a flat, flexible and electrically insulating, anterior lateral base 802. Anterior lateral base 802 may have a lateral line 804, and it may include n antenna elements that may be formed in (e.g., mounted on or built into) anterior lateral base 802 side-by-side, along lateral line 804, where n is an integer equal to or greater than 1. For example, four (n=4) antenna elements, designated as 810, 820, 830, and 840, may be formed in anterior lateral base 802, as demonstrated by FIG. 8. Each of the n antenna elements may have an orientation that may be defined, for example, with respect to the lateral line. Anterior lateral base 802 may be configured such that, when the belt is worn, the n antenna elements formed therein (e.g., antenna element 810, 820, 830, 840) are situated adjacent to, or in front of, the abdomen.

Anterior lateral base 802 may be produced from an isotropically flexible, electrically insulating, material such as Kapton, onto which posterior antenna element 700 is mounted (e.g., laminated), or it be produced from a non-isotropically flexible material that may be based on, or include, for example, Kapton or similar material.

Anterior lateral base 802 may include a base or layer on which antenna elements 810, 820, 830, and 840 may be formed. The output signal of each antenna element 810 through 840 (the radio signal received at each antenna) may be provided, via the pertinent antenna's output terminal, to electrical conductors (e.g., signal traces or electrical wires). The electrical conductors providing the antenna signals may be transferred from anterior lateral base 802 to a receiver, or to a data recorder, via a signal cable that is schematically shown at 850.

Each of antenna elements 810 through 840 may be identical or similar to antenna 600 of FIG. 6 (e.g., antenna elements 810 through 840 may be rectangular). In order to ensure good and stable radio communication between an in-vivo device and an extra-body receiver while the device is in the upper part of the GI system, the orientations of the antenna elements of anterior antenna assembly 800 make up an orientation setup in which each two adjacent antenna elements have different orientations. each of the n antenna elements may have an orientation according to or as per an orientation setup. An example orientation setup is shown in FIG. 8, in which antenna element 810 has an orientation 812, or β1, relative to lateral line 804, that is approximately 45 degrees, and the orientation of antenna element 820 (sown as orientation 822), relative to lateral line 804, is 90 degrees; thus adjacent antenna elements 810 and 820 have different orientations. Likewise, the orientation of antenna element 820, relative to lateral line 804, is 90 degrees, and the orientation of antenna element 830 (sown as orientation 804), relative to lateral line 804, is zero degrees; thus adjacent antenna elements 820 and 830 have different orientations. Likewise, the orientation of antenna element 830, relative to lateral line 804, is zero degrees, and the orientation, β2, of antenna element 840 (sown as orientation 842), relative to lateral line 804, is approximately 135 degrees; thus adjacent antenna elements 830 and 840 have different orientations. Antenna elements 810, 820, 830, and 840 may be asymmetric folded dipole antennas.

In another example orientation setup, the orientation of the n antenna elements is increased by a fixed increment, or delta, Δ, from one antenna element to another. For example, for Δ=40 degrees the orientation of antenna element 810 is 10 degrees, then the orientation of antenna element 820 may be 50 degrees (e.g., 10+40); the orientation of antenna element 830 may be 90 degrees (50+40), and the orientation of antenna element 840 may be 130 degrees (90+40). Δ may have other values. In another example orientation setup, two orientations are used, and the orientation of the n antenna elements alternates across the antenna elements; that is, the orientation of the antenna elements may alternate from one antenna element to another. For example, in a series of n consecutive antenna elements designated as A1, A2, A3, A4, A5, . . . , An, the orientation of the antenna elements may alternate between a first orientation, γ1, and a second orientation, γ2; that is, every odd antenna element (e.g., antenna elements A1, A3, A5, . . . , An2−1) may have orientation γ1 (or orientation γ2), and every even antenna element (e.g., antenna elements A2, A4, A6, . . . , An2) may have orientation γ2 (or orientation γ1). In one example, γ1 may be equal to, say, 45 degrees and γ2 may be equal to, say, 135 degrees. Orientations γ1 and/or γ2 may have different values. Other orientations setups may be used, and an orientation setup may include k orientations (where k is an integer greater than 1), provided that adjacent antenna elements do not have the same orientation.

Although anterior lateral base 802 of FIG. 8 includes four antenna elements, it may include n antenna elements (n may be equal to, or greater than, 1). Each of the antenna elements formed in anterior lateral base 802 may have an orientation that may be defined with respect to lateral line 804, and the orientations of the antenna elements may be optimized to maximize signal reception through the abdomen. Anterior lateral base 802 may be configured, and the antenna elements may be formed therein, such that, when the belt is worn by an individual, the antenna elements lie on the abdomen, or are situated adjacent to or in front of the abdomen, and maximize signal reception through the abdomen.

Similar to antenna element 600 of FIG. 6, each antenna element of anterior lateral assembly 800 may include a ground plane (e.g., similar to ground plane 610 of antenna 600) and a conducting strip (e.g., similar to conducting strip 620 of antenna 600), and the ground plane and the conducting strip may be mounted side-by-side, though other configurations may be used, for example a ground plane and a conducting strip of an antenna element may be mounted in parallel rather than side-by-side. By way of example, antenna element 810 includes a ground plane 814 and a conducting strip 816. Similar to antenna element 600 of FIG. 6, the ground plane of each antenna element of anterior lateral assembly 800 may include a first truncation and the respective conducting strip may include a second truncation, where the second truncation may be situated opposite the first truncation. By way of example, the ground plane and conducting strip of antenna element 820 respectively may include truncations 824 and 826 that may be situated opposite each other. An antenna element of anterior lateral assembly 800 (e.g., antenna elements 810 and 840) may include a truncation in order to enable reducing the width, W2, of anterior lateral assembly 800, while other antenna elements may not have any truncation. Similar to antenna element 600 of FIG. 6, the ground plane of each antenna element of anterior lateral assembly 800 may include a first segment and the conducting strip may include a second segment, where the first segment and the second segment may partly overlap. By way of example, the ground plane and conducting strip of antenna element 830 respectively include partly overlapping segments 832 and 834.

The anterior antenna assembly may further include an anterior pouch (e.g., pouch 922 of FIG. 9) to accommodate anterior antenna assembly 800. The anterior pouch may be releasably connectable or attachable to the belt, for example by using a Velcro fastener. FIG. 8 shows, by way of example, four antenna elements, but other numbers of antenna elements may be used. For example, n may be greater than four (e.g., n=5 or n=6 antenna elements) or less than four antenna elements (e.g., n=3 antenna elements).

A wearable antenna assembly may include a belt that is adapted to be wearable by a person, for example on the person's waist; a first pouch, which is referred to herein as the "posterior pouch", that is adapted to be releasably connected, attached, fastened or tethered to the belt, and to snugly receive, or accommodate, a posterior antenna assembly, such as posterior antenna assembly 722 of FIG. 7D, and a second pouch, which is referred to herein as the "anterior pouch", that is adapted to be releasably connected, attached, fastened or tethered to the belt, and to snugly receive, or accommodate, an anterior antenna assembly, such as anterior antenna assembly 800.

An antenna element formed in posterior base 710 may be referred to as a "posterior antenna", and an antenna element formed in the anterior lateral base 802 may be referred to as an "anterior antenna". The posterior antennas and the anterior antennas may be constructed in the same way or in different ways. For example, a posterior antenna and/or an anterior antenna may include a KAPTON cover layer and a single copper layer. Each of bases 710 and 802 may be laminated to a PORON foam layer or be sandwiched between PORON layers. The layers may tightly be bonded together so that there is no air between the layers. Antenna elements laminated this way (e.g., "sandwiched" antenna elements) are flexible and can easily be deformed to fit to patients having diversified body forms and sizes. 'PORON' is a trade name of a product made by Rogers Corporation. Briefly, PORON is a type of Urethane polymer used for insulating and padding.

Figure 9:
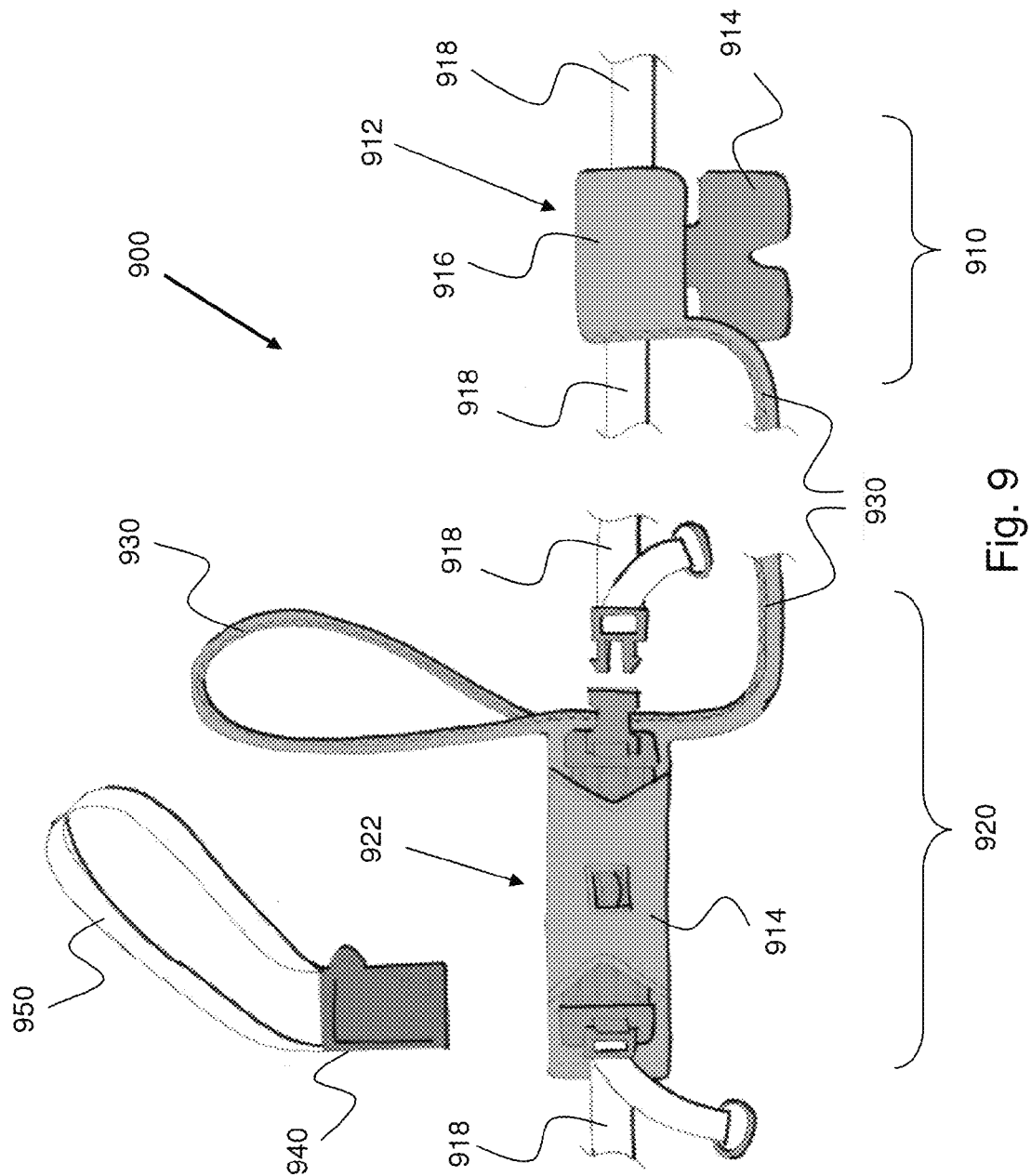
FIG. 9 schematically illustrates a wearable antenna assembly according to an exemplary embodiment.

FIG. 9 schematically illustrates a wearable antenna assembly 900 according to an exemplary embodiment. Wearable antenna assembly 900 includes two distinct sections: a first section 910 that includes a posterior antenna assembly, and a second section 920 that includes an anterior antenna assembly. The posterior antenna assembly and the anterior antenna assembly are not shown in FIG. 9. Each section also includes a pouch that is uniquely adapted to accommodate the pertinent antenna assembly. Section 910 includes a posterior pouch 912 that is releasably attached to a belt 918. Posterior pouch 912 includes a pocket 914 that accommodates the posterior antenna assembly, and a tab 916 attached to belt 918. Anterior pouch 922, which is attached to belt 918, includes a pocket 924 that accommodates the anterior antenna assembly.

The posterior antenna assembly accommodated by pouch 912 may be identical or similar to posterior antenna element 722, and the anterior antenna assembly accommodated by pouch 922 may be identical or similar to anterior antenna assembly 800. Depending on the application, a wearable antenna assembly may include only a posterior antenna assembly (with or without the anterior pouch), or only an anterior antenna assembly (with or without the posterior pouch), or both antenna assemblies. A main signal cable 930 may be connected (e.g., via flat connectors) to the antenna elements of the posterior antenna assembly and anterior antenna assembly and to an external receiver 940 in order to transfer the antenna signals to external receiver 940 (the electrical connection between the wearable antenna assembly and receiver 940 is not shown in FIG. 9). External receiver 940 may be hanged on, or tethered to, the person wearing the antenna assembly, by a carrying/tethering strip 950.

Figure 10:
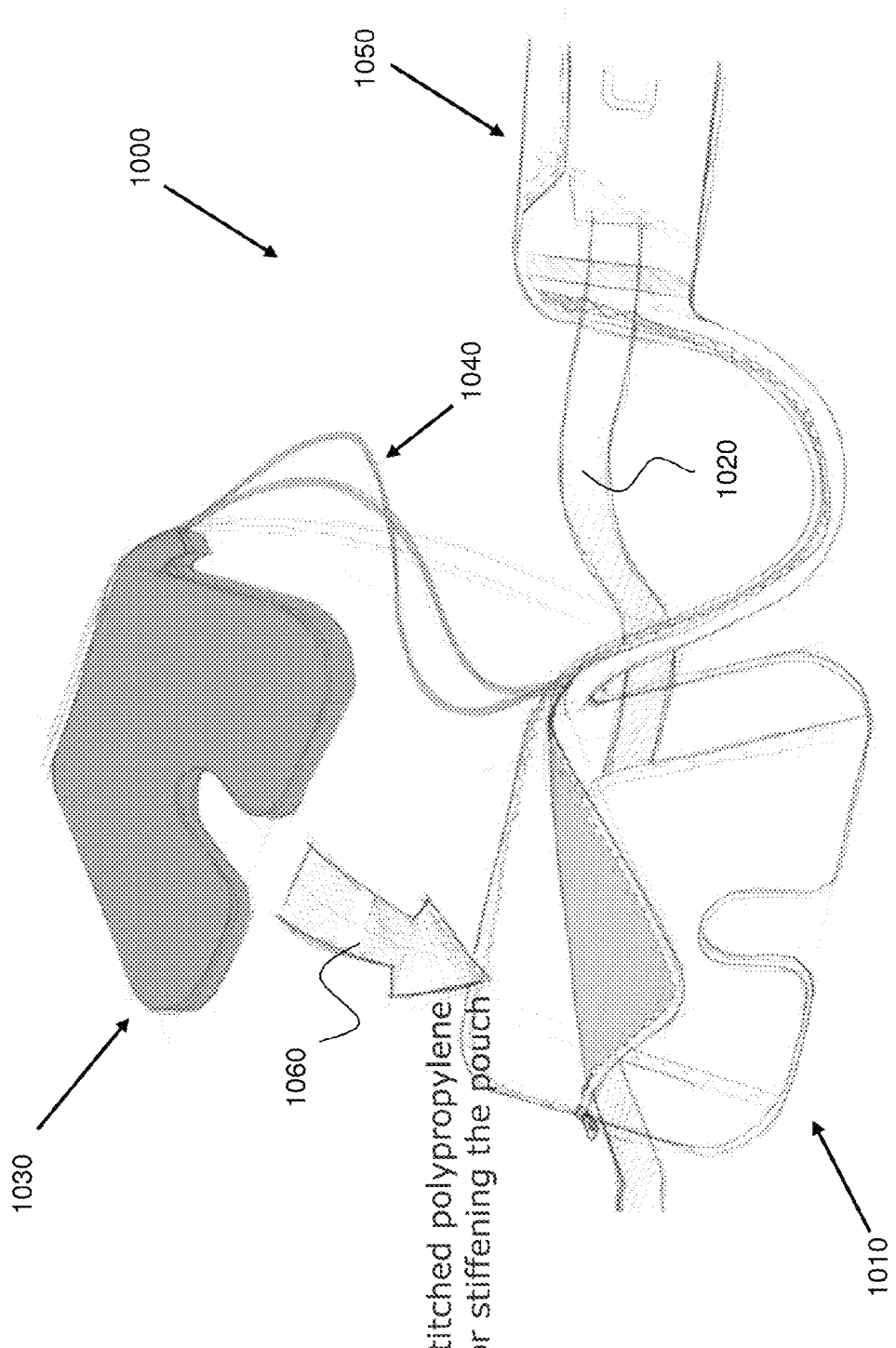
FIG. 10 schematically illustrates a posterior pouch according to an exemplary embodiment.

FIG. 10 schematically illustrates a posterior antenna section 1000 of a wearable antenna assembly according to an exemplary embodiment. Posterior antenna section 1000 includes a posterior pouch 1010 that is attached to a belt 1020, and a posterior antenna assembly 1030 that is shown outside posterior pouch 1010 and may be inserted 1060 into posterior pouch 1010. Cable 1040, which may be similar to cable 715 of FIG. 7D, may transfer radio signals picked up by the antenna elements of the posterior antenna element which is part of posterior antenna assembly 1030. An anterior antenna section of the wearable antenna assembly is partly shown at 1050.

Figure 11:
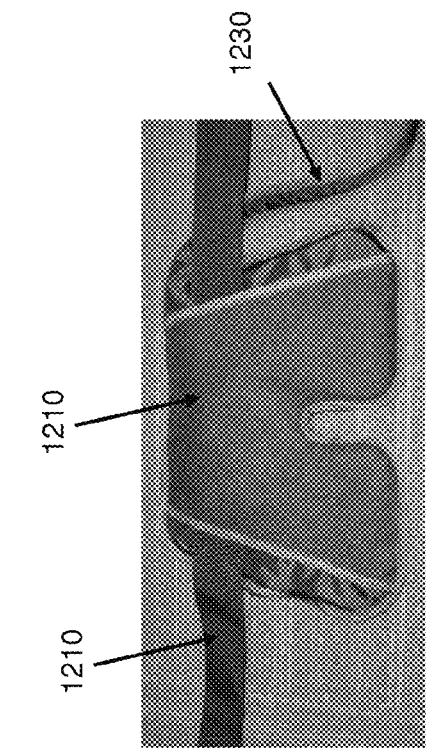
FIG. 11 schematically illustrates a posterior pouch according to another exemplary embodiment.
Figure 12:
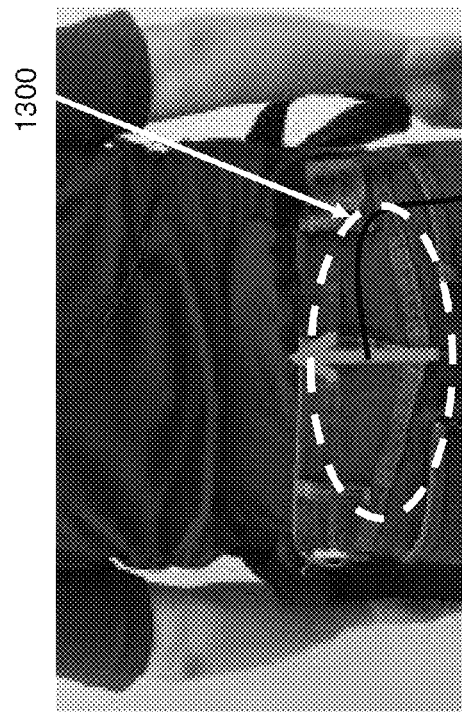
FIG. 12 depicts a posterior pouch connected to a belt according to an exemplary embodiment.
Figure 13A:
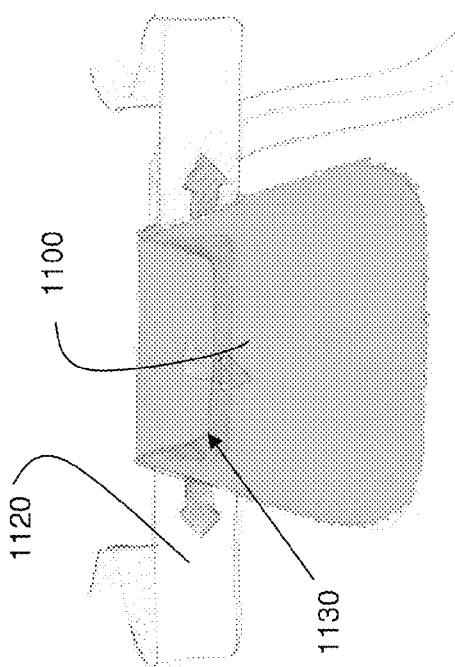
FIGS. 13A-13B depict a worn posterior pouch according to an exemplary embodiment.
Figure 13B:
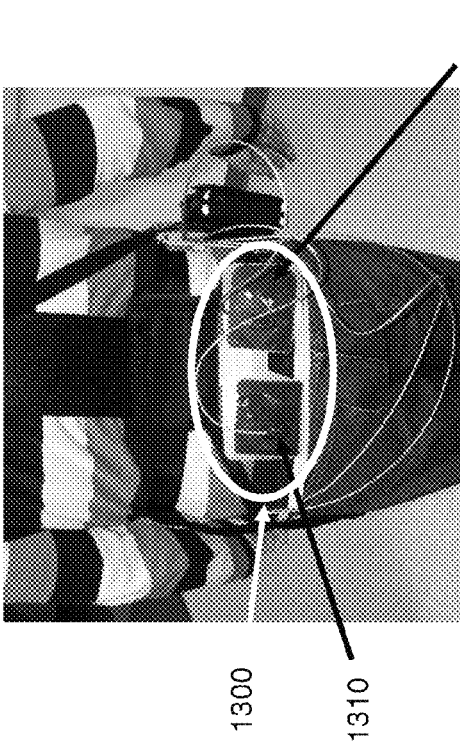

FIG. 11 schematically illustrates a posterior pouch 1100 according to an exemplary embodiment. Posterior pouch 1100 is shown fastened to a belt 1120 by using Velcro type fastener. FIG. 12 depicts a posterior pouch 1210 connected to a belt 1220 according to an exemplary embodiment. Also depicted is a sleeve 1230, through which a signal cable passes. FIGS. 13A-13B depict a worn a posterior antenna assembly (a posterior insert) 1300 according to an exemplary embodiment. Posterior antenna assembly 1300 includes two posterior antennas: posterior antenna 1310 and posterior antenna 1320. Referring to FIG. 13B, the posterior antenna assembly 1310 of FIG. 13A is shown inserted between the body and the trousers. Arrow 1330 points to the belt to which posterior antenna assembly 1300 is connected.

The articles "a" and "an" are used herein to refer to one or to more than one (i.e., to at least one) of the grammatical object of the article, depending on the context. By way of example, depending on the context, "an element" can mean one element or more than one element. The term "including" is used herein to mean, and is used interchangeably with, the phrase "including but not limited to". The terms "or" and "and" are used herein to mean, and are used interchangeably with, the term "and/or," unless context clearly indicates otherwise. The term "such as" is used herein to mean, and is used interchangeably, with the phrase "such as but not limited to".

Having thus described exemplary embodiments of the invention, it will be apparent to those skilled in the art that modifications of the disclosed embodiments will be within the scope of the invention. Alternative embodiments may, accordingly, include more modules, fewer modules and/or functionally equivalent modules. The present disclosure is relevant to various types of in-vivo devices (e.g., in-vivo devices with one or more imagers, -vivo devices with no imagers at all, etc.). Hence the scope of the claims that follow is not limited by the disclosure herein.

The invention claimed is:

1. A wearable antenna assembly to facilitate communication with a swallowable in-vivo device, comprising:
   a posterior antenna assembly comprising:
      a flat posterior antenna element comprising:
         a flat, electrically insulating, posterior base comprising, a lateral portion having a lateral line, and at least a first protrusion continuing from the lateral portion and extending away from said lateral line, and a first antenna element formed in said first protrusion; and a wearable belt to carry the posterior antenna assembly, wherein the at least first protrusion is configured such that, when the belt is worn, the first antenna element is situated adjacent to or in front of a first of the two greater sciatic notches of the pelvis such that the first antenna element is configured to receive a signal from said in-vivo device after said signal travels through said first greater sciatic notch.

2. The antenna assembly as in claim 1, wherein the posterior antenna element further comprises:

a second protrusion; and a second antenna element formed in said second protrusion, said second protrusion continuing the lateral portion and extending away from the lateral line in the same direction as the first protrusion, and wherein the second protrusion is configured such that, when the belt is worn, the second antenna element is situated adjacent to or in front of the second greater sciatic notch of the pelvis such that the second antenna element is configured to receive a signal from said in-vivo device after said signal travels through said second greater sciatic notch.

3. The antenna assembly as in claim 2, wherein the first antenna element and the second antenna element respectively have a first orientation, $\alpha 1$, and a second orientation, $\alpha 2$, relative to the lateral line, wherein $\alpha 1 \neq \alpha 2$.

4. The antenna assembly as in claim 3, wherein $0 \leq \alpha 1 \leq 90$ degrees and $0 \leq \alpha 2 \leq 90$ degrees.

5. The antenna assembly as in claim 2, wherein the first protrusion and the second protrusion are symmetrical about a symmetry line, wherein the symmetry line is substantially perpendicular to the lateral line.

6. The antenna assembly as in claim 5, wherein the posterior antenna assembly further comprises a flat support, to support the posterior antenna element, said support comprising a notch centered on said symmetry line.

7. The antenna assembly as in claim 5, wherein the posterior base is flexible with respect to any of the lateral line and symmetry line, or with respect to both lines.

8. The antenna assembly as in claim 1, wherein the posterior base is isotropically flexible.

9. The antenna assembly as in claim 2, wherein the first antenna element and the second antenna element are generally rectangular.

10. The antenna assembly as in claim 2, wherein the first antenna element and the second antenna element are asymmetric folded dipole antennas.

11. The antenna assembly as in claim 2, wherein each of the first antenna element and the second antenna element includes a ground plane and a conducting strip mounted side-by-side.

12. The antenna assembly as in claim 11, wherein the ground plane includes a first segment and the conducting strip includes a second segment, wherein the first segment and the second segment partly overlap.

13. The antenna assembly as in claim 1, further comprising:

an anterior antenna assembly, comprising:

a flat, electrically insulating, anterior lateral base having a lateral line, and n antenna elements formed, side-by-side, in said anterior lateral base along said lateral line, each antenna element having an orientation defined with respect to the lateral line, wherein the anterior lateral base is configured such that, when the belt is worn, the n antenna elements are situated adjacent to, or in front of, the abdomen.

14. The antenna assembly as in claim 13, wherein each of the n antenna elements is rectangular.

15. The antenna assembly as in claim 13, wherein each two adjacent antenna elements have a different orientation.

16. The antenna assembly as in claim 13, wherein the antenna elements are asymmetric folded dipole antennas.

17. The antenna assembly as in claim 13, wherein each antenna element includes a ground plane and a conducting strip mounted side-by-side.

18. The antenna assembly as in claim 17, wherein the ground plane includes a first segment and the conducting strip includes a second segment, the first segment and the second segment partly overlapping.

19. The antenna assembly as in claim 13, wherein each of the n antenna elements has an orientation as per an orientation setup.

20. The antenna assembly as in claim 19, wherein the orientations of the n antenna elements is increased, from one antenna element to another, by a fixed increment.

21. The antenna assembly as in claim 19, wherein adjacent antenna elements have different orientations.

* * * * *